(12) United States Patent
Yamaguchi et al.

(10) Patent No.: US 10,226,782 B2
(45) Date of Patent: Mar. 12, 2019

(54) CONTENT-ACCOMMODATING CONTAINER, CONTENT-ACCOMMODATING PRODUCT USING SAME, DISCHARGE PRODUCT, AND DISCHARGE DEVICE

(71) Applicant: DAIZO Corporation, Osaka (JP)

(72) Inventors: Kazuhiro Yamaguchi, Kyoto (JP); Kimio Kataoka, Kyoto (JP); Hidetoshi Miyamoto, Kyoto (JP); Satoshi Mekata, Osaka (JP)

(73) Assignee: DAIZO CORPORATION, Osaka (JP)

( * ) Notice: Subject to any disclaimer, the term of this patent is extended or adjusted under 35 U.S.C. 154(b) by 107 days.

(21) Appl. No.: 15/038,277

(22) PCT Filed: Nov. 28, 2014

(86) PCT No.: PCT/JP2014/081583
§ 371 (c)(1),
(2) Date: May 20, 2016

(87) PCT Pub. No.: WO2015/080252
PCT Pub. Date: Jun. 4, 2015

(65) Prior Publication Data
US 2016/0296959 A1 Oct. 13, 2016

(30) Foreign Application Priority Data
Nov. 29, 2013 (JP) .................. 2013-248705

(51) Int. Cl.
*B05B 11/00* (2006.01)
*B05B 15/30* (2018.01)
(Continued)

(52) U.S. Cl.
CPC .......... *B05B 11/3014* (2013.01); *A45D 34/02* (2013.01); *A61L 9/14* (2013.01);
(Continued)

(58) Field of Classification Search
CPC ............ B05B 11/3047; B05B 11/3014; B05B 11/0097; B65D 83/201; B65D 83/32; A45D 34/02; A45D 2200/057
See application file for complete search history.

(56) References Cited

U.S. PATENT DOCUMENTS 3,128,018 A * 4/1964 Cooprider ........... B05B 11/3001
222/153.13
3,217,936 A * 11/1965 Abplanalp ........... B65D 83/646
222/136
(Continued)

FOREIGN PATENT DOCUMENTS

JP 1-258769 A 10/1989
JP 2003-292073 A 10/2003
(Continued)

OTHER PUBLICATIONS

Extended European Search Report issued in European Patent Application 14865825.5, dated Jun. 28, 2017.
(Continued)

*Primary Examiner* — Paul R Durand
*Assistant Examiner* — Randall Gruby
(74) *Attorney, Agent, or Firm* — McDermott Will & Emery LLP

(57) ABSTRACT

This content-accommodating container comprises: a container body having an opening at the top end; and a valve-accommodating part for closing the opening, the valve-accommodating part being fixed to the container body. The valve-accommodating part is provided with: a cylindrical housing part accommodated inside the container body; a tube part extending downward from the housing part, the lower end thereof being disposed near the bottom side of the container body; and a first sealing part for closing the bottom end of the tube part.

8 Claims, 15 Drawing Sheets

(51) Int. Cl.
| | |
|---|---|
| *A45D 34/02* | (2006.01) |
| *A61L 9/14* | (2006.01) |
| *B65D 83/38* | (2006.01) |
| *B65D 83/42* | (2006.01) |
| *B65D 83/44* | (2006.01) |
| *B65D 83/20* | (2006.01) |
| *B65D 83/32* | (2006.01) |
| *B65D 83/22* | (2006.01) |
| *B65D 83/48* | (2006.01) |

(52) U.S. Cl.
CPC ...... *B05B 11/0037* (2013.01); *B05B 11/0097* (2013.01); *B05B 11/3047* (2013.01); *B05B 11/3059* (2013.01); *B05B 15/30* (2018.02); *B65D 83/20* (2013.01); *B65D 83/201* (2013.01); *B65D 83/22* (2013.01); *B65D 83/32* (2013.01); *B65D 83/38* (2013.01); *B65D 83/42* (2013.01); *B65D 83/44* (2013.01); *B65D 83/48* (2013.01); *A45D 2200/057* (2013.01); *A61L 2209/134* (2013.01)

(56) References Cited

U.S. PATENT DOCUMENTS

| | | | | | |
|---|---|---|---|---|---|
| 3,241,722 | A | * | 3/1966 | Nissen | B65D 83/34 222/136 |
| 3,272,389 | A | * | 9/1966 | Frangos | B65D 83/68 222/136 |
| 3,454,198 | A | * | 7/1969 | Flynn | B65D 83/306 137/614.11 |
| 3,731,847 | A | * | 5/1973 | Webster | B65D 83/682 222/136 |
| 3,761,022 | A | * | 9/1973 | Kondo | B05B 11/3039 222/385 |
| 4,072,247 | A | * | 2/1978 | Yamazaki | B01L 3/0282 222/309 |
| 4,417,674 | A | * | 11/1983 | Giuffredi | B65D 83/48 222/402.18 |
| 4,801,049 | A | * | 1/1989 | Thompson | B05B 11/0027 222/179.5 |
| 4,821,923 | A | * | 4/1989 | Skorka | B05B 11/0081 222/80 |
| 5,064,102 | A | * | 11/1991 | Montaner | B05B 11/0013 222/147 |
| 5,096,094 | A | * | 3/1992 | Guilbert | B05B 11/3001 222/153.13 |
| 5,167,347 | A | * | 12/1992 | Wiegner | B65D 83/46 222/136 |
| 5,271,530 | A | * | 12/1993 | Uehira | B05B 7/0037 222/190 |
| 5,273,189 | A | * | 12/1993 | Jouillat | B05B 11/0005 222/80 |
| 5,388,766 | A | * | 2/1995 | Buisson | B05B 1/3436 222/321.2 |
| 5,570,819 | A | * | 11/1996 | Uehira | B05B 7/0037 222/190 |
| 5,695,096 | A | * | 12/1997 | Yquel | B65D 83/34 222/402.18 |
| 5,769,274 | A | * | 6/1998 | Behar | B05B 11/3025 222/95 |
| 6,328,543 | B1 | * | 12/2001 | Benecke | A47L 13/20 222/383.1 |
| 6,481,435 | B2 | * | 11/2002 | Hochrainer | A61K 9/0078 128/200.14 |
| 6,598,762 | B2 | * | 7/2003 | McKune | B65D 83/666 222/129 |
| 6,681,962 | B2 | * | 1/2004 | Masuda | B05B 11/3023 222/321.7 |
| 6,742,677 | B2 | * | 6/2004 | Petit | B05B 11/0059 222/321.7 |
| 6,923,346 | B2 | * | 8/2005 | Foster | B05B 7/0031 222/145.5 |
| 7,213,593 | B2 | * | 5/2007 | Hochrainer | A61J 1/2093 128/200.14 |
| 7,455,195 | B2 | * | 11/2008 | Mekata | B05B 11/0043 222/105 |
| 8,857,671 | B2 | * | 10/2014 | Muller | B05B 11/3052 222/321.9 |
| 9,834,369 | B2 | * | 12/2017 | Lamboux | B65D 83/14 |
| 2005/0279774 | A1 | * | 12/2005 | Kuwahara | B05B 11/3025 222/383.1 |
| 2007/0158367 | A1 | * | 7/2007 | Lin | B05B 11/3001 222/321.7 |
| 2008/0135581 | A1 | * | 6/2008 | Kennedy | B05B 11/3009 222/205 |
| 2010/0098480 | A1 | * | 4/2010 | Byeon | B05B 11/3053 401/136 |
| 2012/0104049 | A1 | * | 5/2012 | Choquart | B05B 11/3042 222/321.9 |
| 2012/0267399 | A1 | * | 10/2012 | Moretti | B05B 11/3008 222/321.2 |
| 2013/0200106 | A1 | * | 8/2013 | Kang | B65D 55/02 222/153.13 |
| 2014/0008389 | A1 | * | 1/2014 | Mekata | B65D 83/20 222/94 |
| 2014/0314600 | A1 | * | 10/2014 | Ding | B05B 11/3023 417/437 |
| 2015/0166253 | A1 | * | 6/2015 | Nomura | B65B 31/003 222/402.1 |
| 2015/0251203 | A1 | * | 9/2015 | Wang | B05B 11/3001 222/153.13 |
| 2015/0284175 | A1 | * | 10/2015 | Lamboux | B65D 83/14 222/1 |

FOREIGN PATENT DOCUMENTS

| | | |
|---|---|---|
| JP | 2008-110802 A | 5/2008 |
| JP | 4365467 B2 | 11/2009 |
| JP | 2014-091527 A | 5/2014 |
| WO | 200130668 A1 | 5/2001 |
| WO | 2002060995 A2 | 8/2002 |

OTHER PUBLICATIONS

International Search Report issued in International Application No. PCT/JP2014/081583, dated Mar. 3, 2015, with English Translation.

* cited by examiner

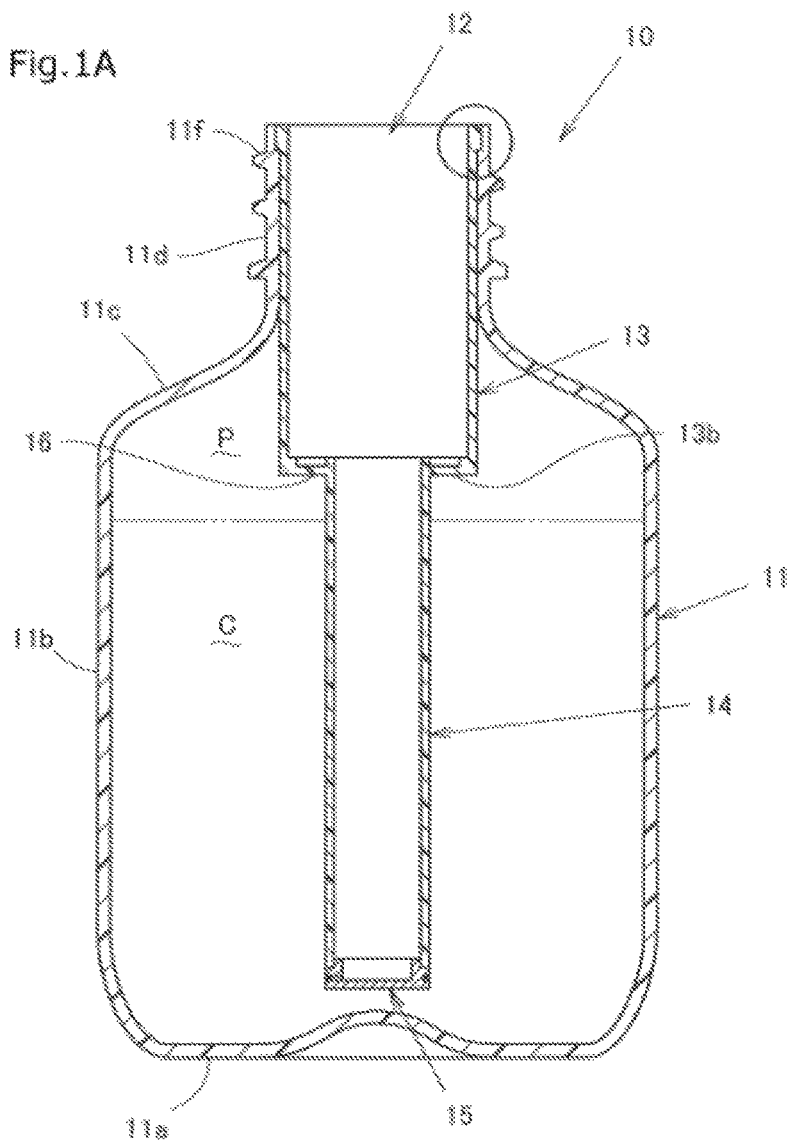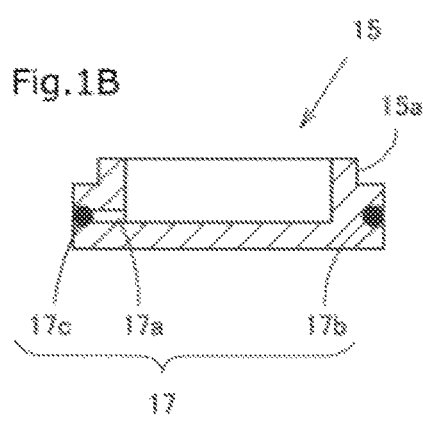

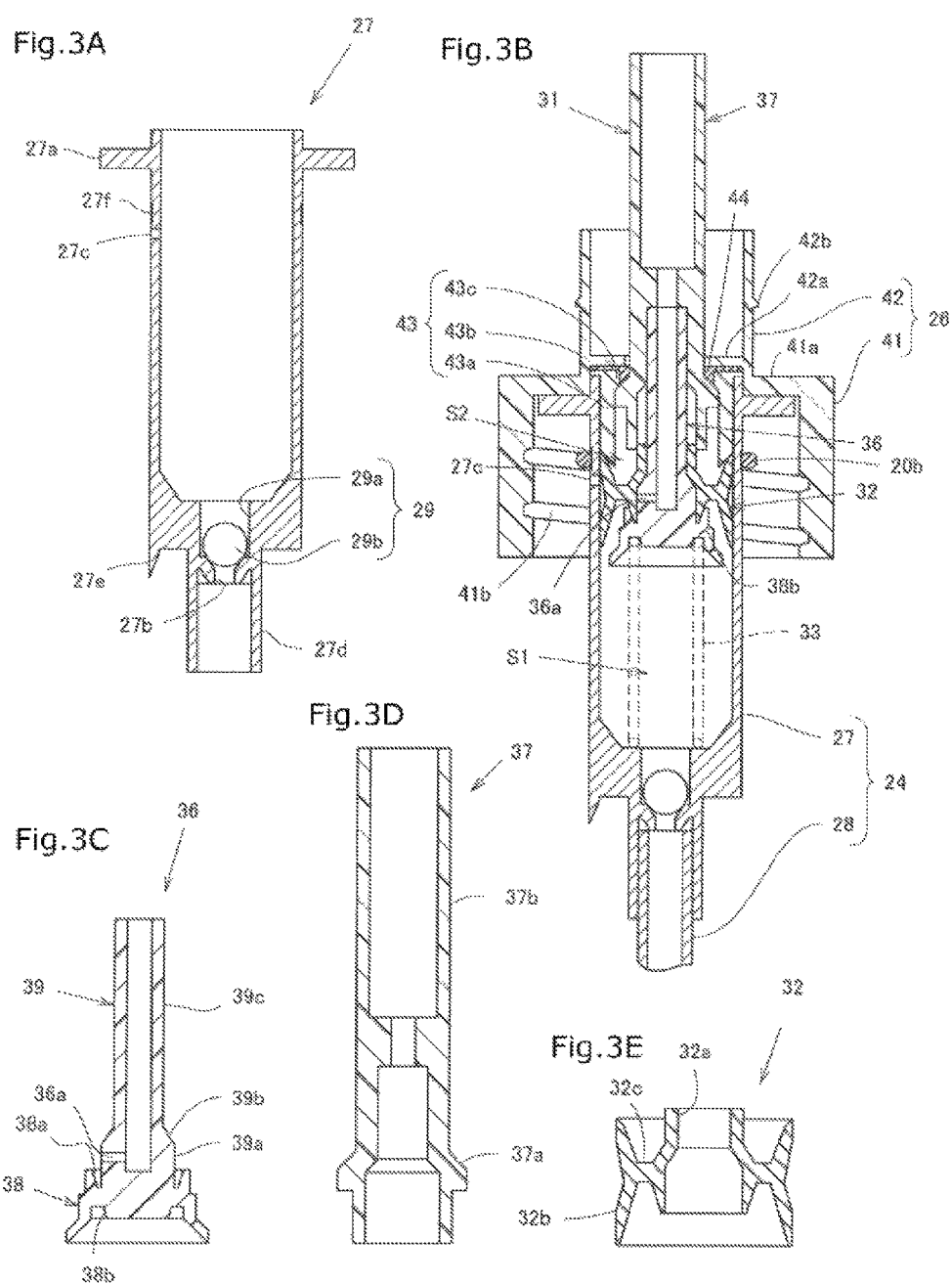

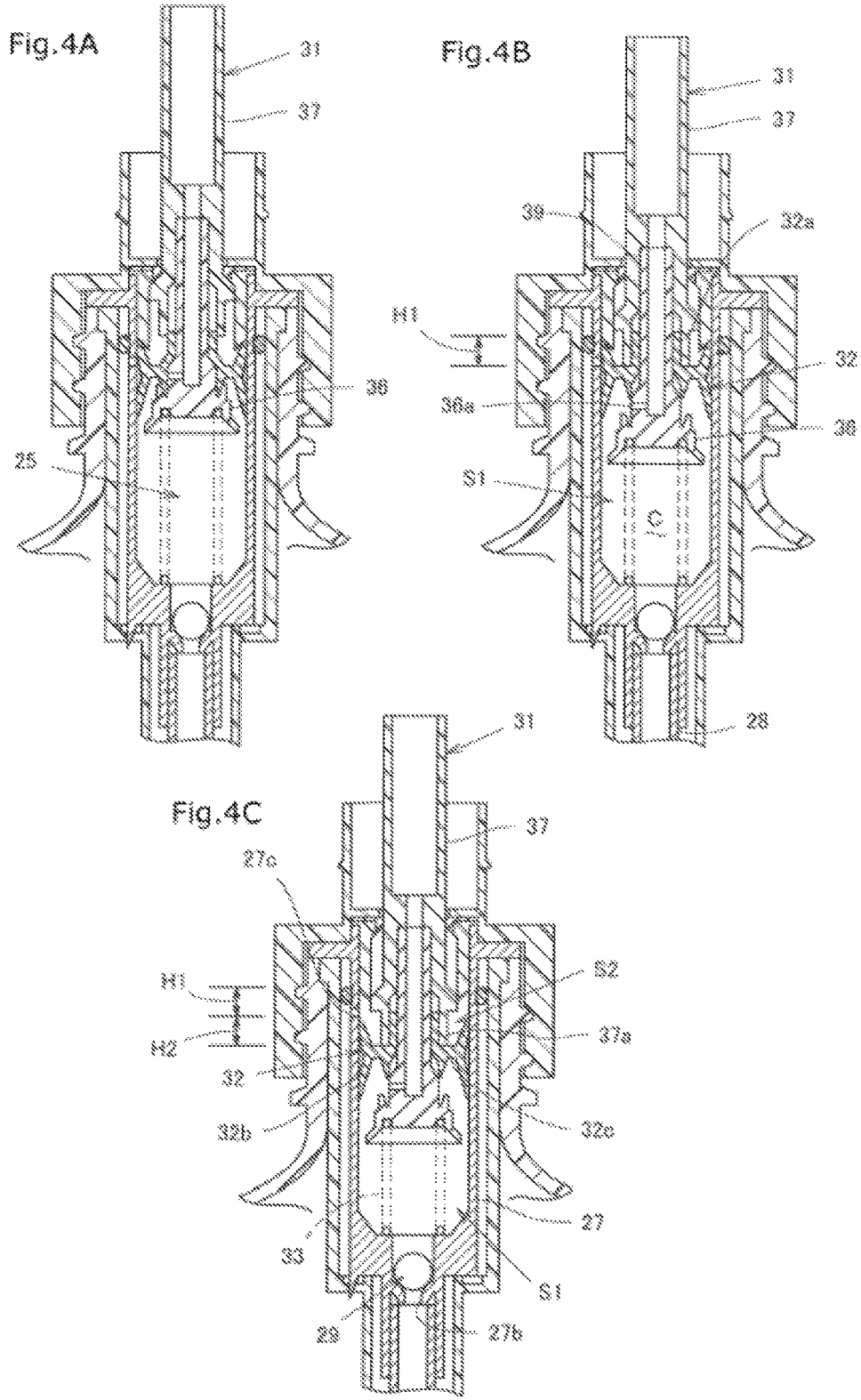

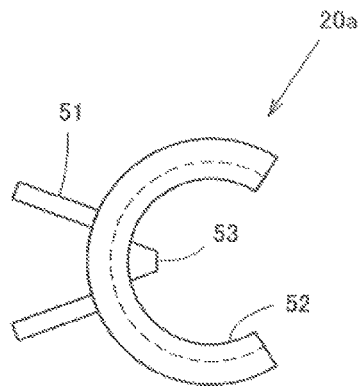
Fig.5A
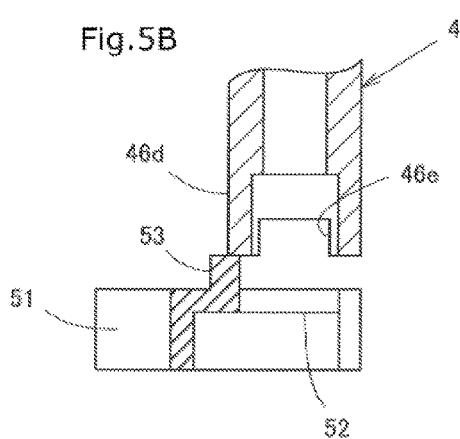
Fig.5B
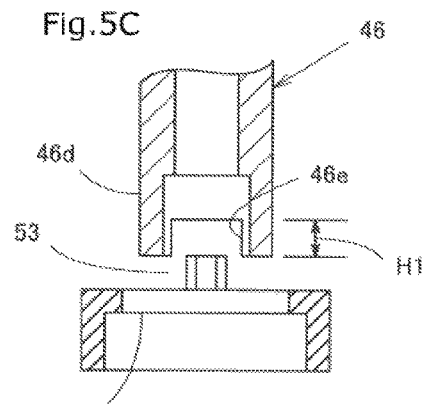
Fig.5C
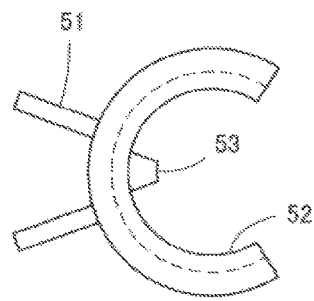
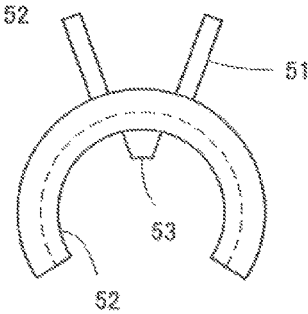

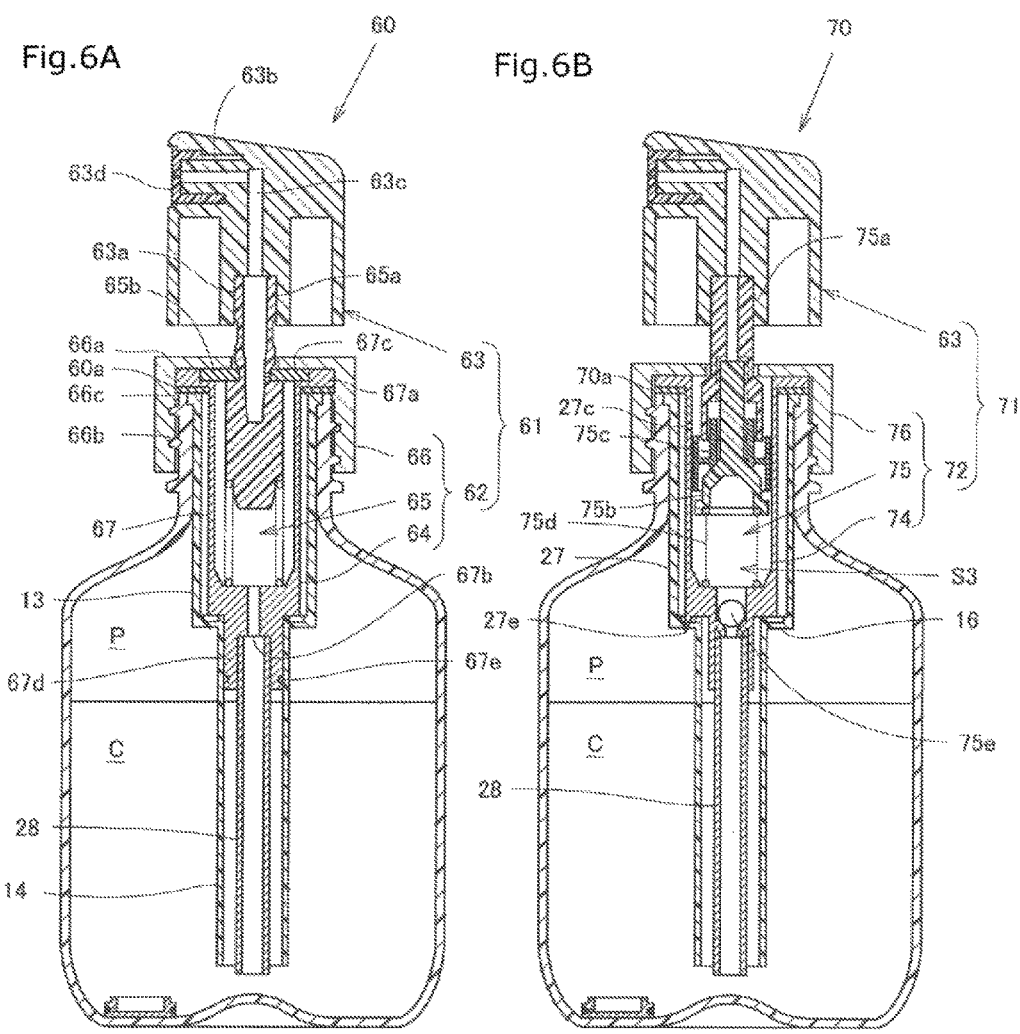

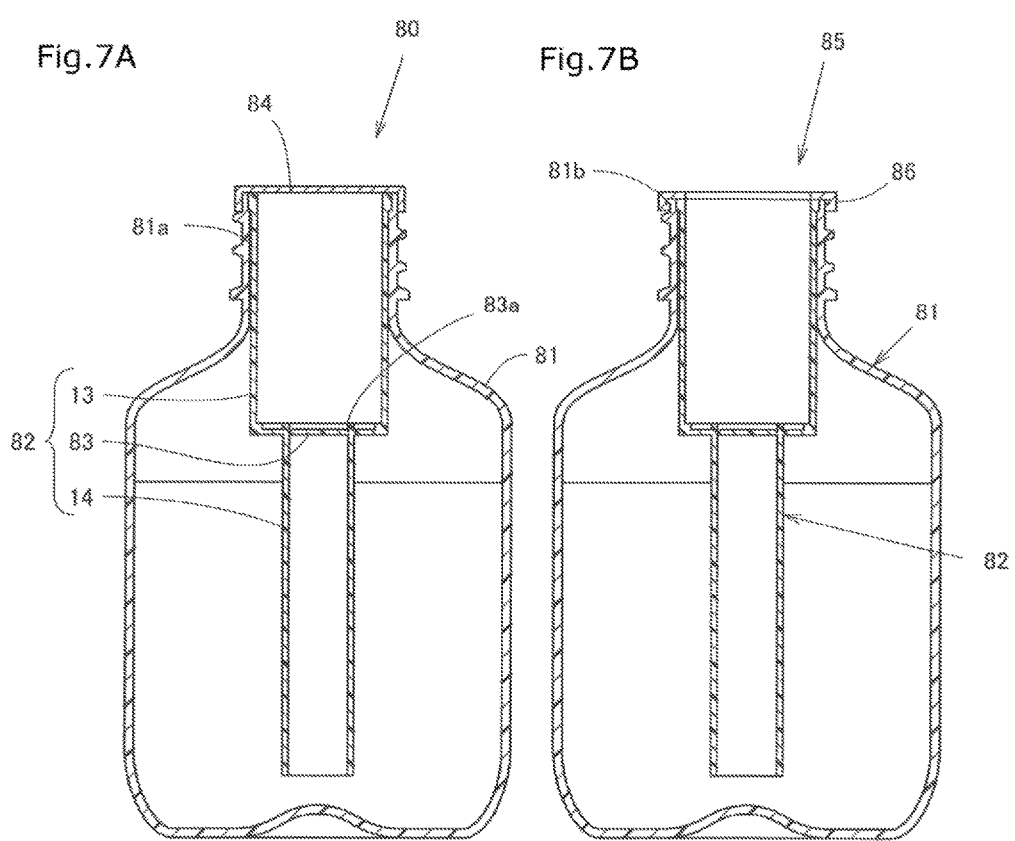

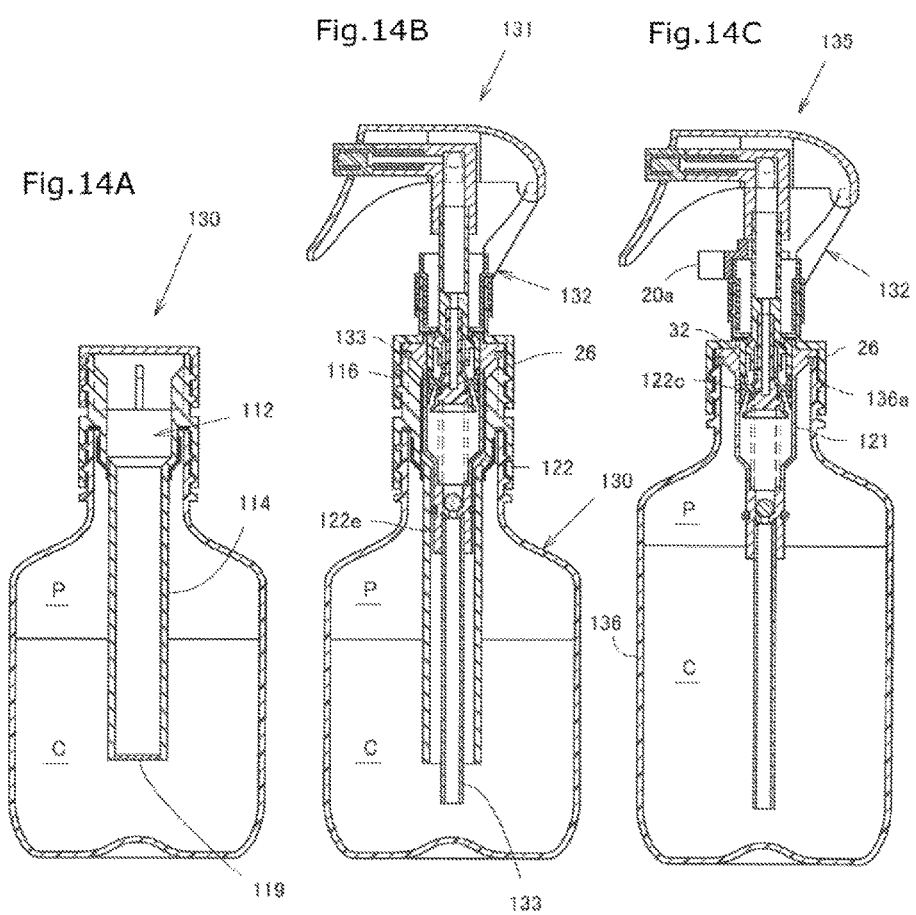

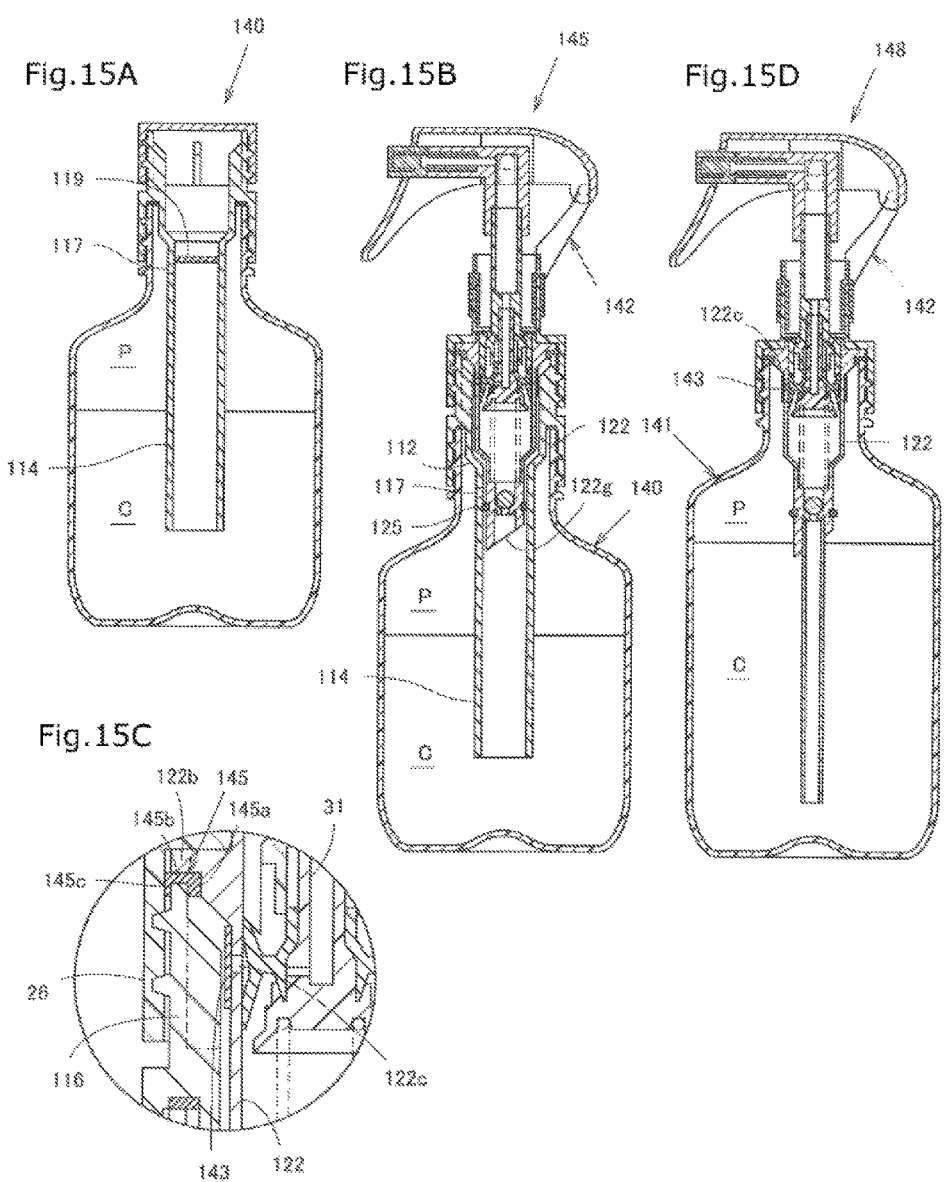

CONTENT-ACCOMMODATING CONTAINER, CONTENT-ACCOMMODATING PRODUCT USING SAME, DISCHARGE PRODUCT, AND DISCHARGE DEVICE

RELATED APPLICATIONS

This application is the U.S. National Phase under 35 U.S.C. § 371 of International Application No. PCT/JP2014/081583, filed on Nov. 28, 2014, which in turn claims the benefit of Japanese Application No. 2013-248705, filed on Nov. 29, 2013, the disclosures of which Applications are incorporated by reference herein.

FIELD OF INVENTION

The present invention relates to a content-accommodating container, a content-accommodating product using the same, a discharge product, and a discharge device. For details, it relates to a refill content-accommodating container in which a discharge device equipped with a valve mechanism is usable repeatedly, and a content-accommodating product, a discharge device using the same.

DESCRIPTION OF BACKGROUND ART

Recently, while ecology is advocated, in many discharge products, contents of discharge containers are filled in simple containers and are sold. For example, in a spray product with a pump, which sprays fragrance and deodorant to room interiors and furniture, it has become main stream that which consists of a container with a pump in which a concentrate is filled, and a pouch in which a refill concentrate is filled. And, when the concentrate in a container has run out, the concentrate is replenished from the pouch after detaching the pump, and by attaching the pump, the container with the pump can be reused.

Moreover, in Patent Document 1, a container with a pump is disclosed, in which a composition for a dispenser is filled in the container, where the composition is made so that nitrogen gas of a quantity of which the saturated pressure is 0.2-2.0 ($kg/cm^2$-G) is dissolved in a hydrated composition.

Further, an aerosol container in which a pressurizing agent and a concentrate is filled is known.

PRIOR ART DOCUMENTS

Patent Documents

Patent Document 1: Japanese published Patent Document 4365467

DESCRIPTION OF THE INVENTION

Problems to be Solved

However, in the container with a pump or the aerosol container of Patent Document 1, since the concentrate is sealed in a state pressurized by a pressuring agent, it is not possible for users to use the container by replacing a pump valve or an aerosol valve.

The present invention is aimed to provide a refill content-accommodating container of a pressurized content (a concentrate and a pressurizing agent), and a content-accommodating product, a discharge product using the content-accommodating container.

Means of Solving the Problem

The content-accommodating container of the present invention is a content-accommodating container for accommodating a concentrate and a pressurizing agent, which is characterized in that it is unsealed and used by attaching a removable valve member having a valve mechanism, comprising a container body having an opening, and a tubular valve accommodating portion for accommodating the valve mechanism, being fixed to the container body closing the opening of the container body, in which the valve accommodating portion has a communicating portion to communicate with a liquid phase of the container body and a first unsealing portion to close the communicating portion.

In the content-accommodating container of the present invention, it is preferable that the valve accommodating portion is provided with a tubular housing portion which accommodates the valve mechanism, being fixed to the opening of the container body, a tube portion extending downward from the housing portion, communicating with the liquid phase of the container body at the lower end thereof, and the first unsealing portion which closes the housing portion or the tube portion.

In the content-accommodating container of the present invention, it is preferable that the inside of the valve accommodating portion has a second unsealing portion for forming a gas introducing passage to communicate with a gas phase of the container body.

In the content-accommodating container of the present invention, it is preferable that the valve accommodating portion is provided with the gas introducing passage communicating with the gas phase of the container body, and a check valve which closes the gas introducing passage, allows a fluid flow to the container body, and blocks a fluid flow to the exterior.

In the content-accommodating container of the present invention, it is preferable that the first unsealing portion is provided in a position corresponding to the lower end of the valve member, when the valve member is attached.

In the content-accommodating container of the present invention, it is preferable that the first unsealing portion is provided with a check valve for filling a pressurizing agent, which allows a fluid flow to the container body, and blocks a fluid flow to the exterior.

In the content-accommodating container of the present invention, it is preferable that the valve accommodating portion is provided with a valve cap portion which extends outward in the radial direction from the upper end of the housing portion, and extends downward from the end portion thereof so as to cover the outer periphery of the container body, and fits in the outer periphery of the container body with the inner surface thereof, and further, a tubular attaching portion extending upward from the valve cap portion.

The content-accommodating product of the present invention is characterized in that it comprises the content-accommodating container of the present invention, and the concentrate and the pressurizing agent filled in the content-accommodating container.

The discharge product of the present invention is characterized in that it comprise the content-accommodating product and a discharge device attached to the content-accommodating container, in which the discharge device is provided with the valve member comprising a valve housing accommodated in the valve accommodating portion, the valve mechanism accommodated in the valve housing, and the cap which fixes the valve housing to the content-accommodating container, and in which the valve housing has the first unsealing mechanism to unseal the first unsealing portion of the content-accommodating container.

In the discharge product of the present invention, it is preferable that the valve housing has the second unsealing mechanism which unseals the second unsealing portion of the content-accommodating container. In the discharge product of the present invention, it is preferable that the valve mechanism is an aerosol valve mechanism. In this case, it is preferable that the valve mechanism is provided with an auxiliary pump mechanism to compress a storing space of contents in the valve housing. Further, it is preferable that the auxiliary pump mechanism comprises the valve housing and a piston which slides inside the valve housing in conjunction with the stem, when the stem of the aerosol valve mechanism is pushed down more than a prescribed amount. In this case, it is preferable that a gas phase communicating hole which communicates the gas phase of the container body with the exterior is formed in the valve housing, and in which the gas phase communicating hole is closed by the piston, when the auxiliary pump is not operating, and is opened by the operation of the piston. In addition, a switching mechanism to operate the auxiliary pump mechanism may be provided. Further, it is preferable that there is provided a seal material which is compressed in the radial direction between the outer surface of the valve housing and the inner surface of the valve accommodating portion.

In the discharge product of the present invention, it is preferable that the valve mechanism is a pump valve.

The discharge device of the present invention attached to the content-accommodating container for accommodating a concentrate and a pressurizing agent is characterized in that it is provided with a valve member comprising a valve housing accommodated in a content-accommodating container, a valve mechanism accommodated in the valve housing, and a cap which fixes the valve housing to the content-accommodating container, in which the valve mechanism is provided with an aerosol valve mechanism, an auxiliary pump mechanism which compresses a storing space of the concentrate in the valve housing portion, and a switching mechanism to operate the auxiliary pump mechanism, and in which the valve housing has a first unsealing mechanism which unseals the first unsealing portion communicating with a liquid phase portion of the content-accommodating container.

In the discharge device of the present invention, it is preferable that there is provided a seal material which is compressed in the radial direction between the outer surface of the valve housing and the inner surface of the content-accommodating container.

In the discharge device of the present invention, it is preferable that the auxiliary pump mechanism comprises the valve housing and a piston which slides inside the valve housing in conjunction with the stem, when the stem of the aerosol valve mechanism is pushed down more than a prescribed amount. In this case, it is preferable that a gas phase communicating hole which communicates the gas phase of the container body with the exterior is formed in the valve housing, and in which the gas phase communicating hole is closed by the piston, when the auxiliary pump mechanism is not operating, and is opened by the operation of the piston.

Effect of the Invention

A content-accommodating container of the present invention for accommodating a concentrate and a pressurizing agent, which is unsealed and used by attaching a removable valve member having a valve mechanism, comprises a container body having an opening, and a tubular valve accommodating portion for accommodating the valve mechanism, being fixed to the container body closing the opening of the container body, in which the valve accommodating portion is provided with a communicating portion to communicate with a liquid phase of the container body and a first unsealing portion to close the communicating portion. Therefore, it is possible to store the concentrate stably for a long period preventing the invasion of external oxygen and bacteria by the pressure of the pressurizing agent. Moreover, since it is provided with the valve accommodating portion to accommodate the valve mechanism, and is provided with the first unsealing portion unsealed when the valve member is attached in the communicating portion communicating with the liquid phase of the container body, the pressurizing agent is hard to leak out to the exterior, even if the first unsealing portion is unsealed when the valve member (discharge device) is attached. In other words, the valve member (discharge device) is easy to be attached, which is preferable as a refill container of contents having a pressure. Hence, the discharge device equipped with the valve member for this content-accommodating container can be used repeatedly.

In the content-accommodating container of the present invention, in the case that the valve accommodating portion accommodates the valve mechanism, and is provided with a tubular housing portion which accommodates the valve mechanism, being fixed to the opening of the container body, the tube portion extending downward from the housing portion, communicating with the liquid phase of the container body at the lower end thereof, and the first unsealing portion which closes the housing portion or the tube portion, it is possible to hold the valve member (discharge device) with the housing portion when in attaching, the first unsealing portion is easy to be unsealed. Moreover, since the tube portion provided below the housing portion is communicated with the liquid phase of the container body, it is possible to prevent the pressurizing agent from leaking out, when the first unsealing portion is unsealed (when the valve member (discharge device) is attached).

In the content-accommodating container of the present invention, in the case that the inside of the valve accommodating portion has the second unsealing portion for forming the gas introducing passage communicating with the liquid phase of the container body, it is preferable as the refill container of the discharge device equipped with the pump mechanism.

In the content-accommodating container of the present invention, when the valve accommodating portion is equipped with the gas introducing passage communicating with the gas phase of the container body, and a check valve which allows the fluid flow to the container body and blocks the fluid flow to the exterior, it is possible to prevent the pressurizing agent filled in the container body from exhausted.

In the content-accommodating container of the present invention, in the case that the first unsealing portion is provided in a position corresponding to the lower end of the valve member, when the valve member is attached, since the first unsealing portion is apart from the opening of the container body, it is possible to unseal the first unsealing portion while closing the valve accommodating portion with the valve member, the concentrate and the pressurizing agent are hard to leak out to the exterior when unsealing. Particularly, by unsealing the first unsealing portion after securing the airtightness inside the valve accommodating portion (housing portion) with the valve member, it is possible to prevent completely the concentrate and the pressurizing agent from leaking out. Hence, it is possible to discharge utilizing the pressurizing agent, and is possible to make a refill container which produces an arbitrary discharge (or spray) configuration accurately.

In the content-accommodating container of the present invention, in the case that the first unsealing portion is equipped with the check valve which allows the fluid flow to the container body and blocks the fluid flow to the exterior, it is possible to fill the pressuring agent after attaching the valve accommodating portion to the container body, and sealing the content-accommodating container, the manufacture of the product is easy. In the content-accommodating container of the present invention, in the case that the valve accommodating portion is provided with the valve cap portion which protrudes outward in the radial direction from the upper end of the housing portion, extends downward so as to cover the outer periphery of the container body from the end portion thereof, and fits in the outer periphery of the container body with the inside surface thereof, and further the tubular attaching portion extending upward from the valve cap portion, since the attaching portion independent to the fitting/fixing of the valve accommodating portion and the container body is provided, when replacing the discharge device, the fitting of the container body and the valve accommodating portion never becomes loose. Hence, it is possible for users to replace the discharge device safely, not giving consideration to the fixed state of the container body and the valve accommodating portion.

Since the content-accommodating product of the present invention comprises the content-accommodating container of the present invention and the concentrate and the pressurizing agent filled in the content-accommodating container, it can be made to be a refill product accommodating pressurized contents Since the discharge device of the present invention comprises the content-accommodating product and the discharge device attached to the content-accommodating container, the discharge device is provided with the valve member comprising a valve housing accommodated in the valve accommodating portion, the valve mechanism accommodated in the valve housing, and the cap which fixes the valve housing to the content-accommodating container, and the valve housing has the first unsealing portion to unseal the first unsealing portion of the content-accommodating container, it is possible to fix the valve housing to the content-accommodating container almost at the same time when the valve housing is inserted into the valve accommodating portion. Hence, escaping of the pressurizing agent can be prevented allowing the stable production of the discharge device utilizing the pressurizing agent. And, this discharge product can be reused repeatedly. Particularly, in the case that when the valve housing is inserted into the valve accommodating portion and is fixed with the cap, and the first unsealing portion is unsealed after securing airtightness of the valve accommodating portion, it is possible to prevent completely the concentrate and the pressurizing agent from leaking out.

In the discharge product of the present invention, in the case that the valve housing has the second unsealing mechanism to unseal the second unsealing portion of the content-accommodating container, it becomes possible to reuse the discharge device equipped with the pump mechanism. In the discharge product of the present invention, even if the valve mechanism is the aerosol valve mechanism or the auxiliary pump mechanism, it is possible to reuse the discharge device.

In the discharge product of the present invention in which the valve mechanism is the aerosol valve, in the case that the auxiliary pump mechanism which compresses the storing space of the concentrate in the valve housing is provided, in the beginning of use, the concentrate can be discharged in a preferable state such as continuous discharge using a pressurizing agent making the concentrate so as to be in an aerosol discharge state, and when the aerosol discharge state becomes worse (the impetus of discharge or spray becomes weak) due to the lowering of the inner pressure, by assisting the discharge of the concentrate with the auxiliary pump mechanism, it is possible to discharge the concentrate in a preferable state to the last. Particularly, it is preferable that the discharge state is in a spray state.

Moreover, in the case that the auxiliary pump comprises the valve housing and the piston which slides inside the valve housing in conjunction with the stem, when the stem of the aerosol valve mechanism is pushed down more than a prescribed amount, it is possible to bring the auxiliary pump mechanism into operation by the amount of pushing down.

Further, in the discharge product of the present invention provided with the auxiliary pump mechanism, a gas phase communicating hole which communicates the gas phase of the container body with the exterior is formed in the valve housing, and in which the gas phase communicating hole is closed by the piston, when the auxiliary pump mechanism is not operating, and is opened by the operation of the piston, it is possible to prevent the pressurizing agent to be discharged when the auxiliary pump mechanism is not operated.

In addition, in the case that the valve mechanism is provided with a switching mechanism to operate the auxiliary pump mechanism, it is possible to prevent the malfunction of the auxiliary pump mechanism.

In the discharge product of the present invention, in the case that there is provided a seal material which is compressed in the radial direction between the outer surface of the valve housing and the inner surface of the valve accommodating portion, since the sealability can be secured, even if the seal material makes vertical motion to the valve housing or the valve accommodating portion, when attaching the discharge device to the content-accommodating product, it is possible to unseal the unsealing portion while keeping the sealability, the pressurizing agent is hard to leak out, making the replacement easy.

In the discharge product of the present invention, there is provided the seal material which is compressed in the vertical direction between the cap and the upper end of the container body, it is possible to prevent the pressurizing agent from leaking out from between the valve accommodating portion and the container body.

In the discharge product of the present invention, a discharge device attached to the content-accommodating container for accommodating a concentrate and a pressurizing agent is provided with a valve member comprising a valve housing accommodated in a content-accommodating container, a valve mechanism accommodated in the valve housing, and a cap which fixes the valve housing to the content-accommodating container, in which the valve mechanism is provided with an aerosol valve mechanism, an auxiliary pump mechanism which compresses a storing space of a concentrate in the valve housing portion, and a switching mechanism to operate the auxiliary pump mechanism, and in which the valve housing has a first unsealing mechanism which unseals the first unsealing portion communicating with a liquid phase portion of the content-accommodating container, Therefore, it is repeatedly usable to the content-accommodating products for refill products.

In the discharge product of the present invention, in the case that there is provided a seal material which is compressed between the outer surface of the valve housing and the inner surface of the content-accommodating container in the radial direction, it is easily attached to the content-accommodating products for refill products.

In the discharge product of the present invention, in the case that auxiliary pump mechanism comprises the valve housing and the piston which slides inside the valve housing in conjunction with the stem, when the stem of the aerosol valve mechanism is pushed down more than a prescribed amount, it is possible to bring the auxiliary pump mechanism into operation by the amount of pushing down, and it is easy to use.

In the discharge product of the present invention provided with the auxiliary pump mechanism, a gas phase communicating hole which communicates the gas phase of the container body with the exterior is formed in the valve housing, and in which the gas phase communicating hole is closed by the piston, when the auxiliary pump is not operating, and is opened by the operation of the piston, it is possible to prevent the pressurizing agent from discharged to the exterior, when the auxiliary pump mechanism is not operated.

BRIEF DESCRIPTION OF THE DRAWINGS

FIG. 1A is a cross-sectional view showing one embodiment of the content-accommodating container of the present invention, FIG. 1B is a cross-sectional view showing the closing portion thereof, FIG. 1C is a partial enlarged view thereof;

FIG. 3A is a cross-sectional view of the valve housing of the discharge product of FIG. 2, FIG. 3B is a cross-sectional view showing the valve mechanism of the discharge product of FIG. 2, FIG. 3C is a cross-sectional view showing the internal stem thereof, FIG. 3D is a cross-sectional view showing the external stem thereof, FIG. 3E is a cross-sectional view showing the piston thereof;

FIG. 4A-C are cross-sectional views showing the stopped state, the aerosol discharging state, and the pump discharging state of the valve mechanism of the discharge product of FIG. 2 respectively;

FIG. 5A is a plain view showing the operation switching member of the discharge product of FIG. 2, FIG. 5B, 5C are cross-sectional views showing the operation switching state;

FIG. 6A, B are cross-sectional views showing another embodiment of the discharge product of the preset invention respectively;

FIG. 7A, FIG. 7B are cross-sectional views showing another embodiment of the content-accommodating container of the preset invention respectively;

FIG. 14A, B are cross-sectional views showing another aspect of the content-accommodating container and the discharge product of the present invention respectively, FIG. 14C is a cross-sectional view of the discharge product using the discharge device of the present invention;

FIG. 15A, B are cross-sectional views showing another aspect of the content-accommodating container and the discharge product of the present invention respectively, FIG. 15C is a cross-sectional view enlarging a part of FIG. 15B, FIG. 15D is a cross-sectional view of the discharge product using the discharge device of the present invention.

EMBODIMENT FOR CARRYING OUT THE INVENTION

Figure 2:
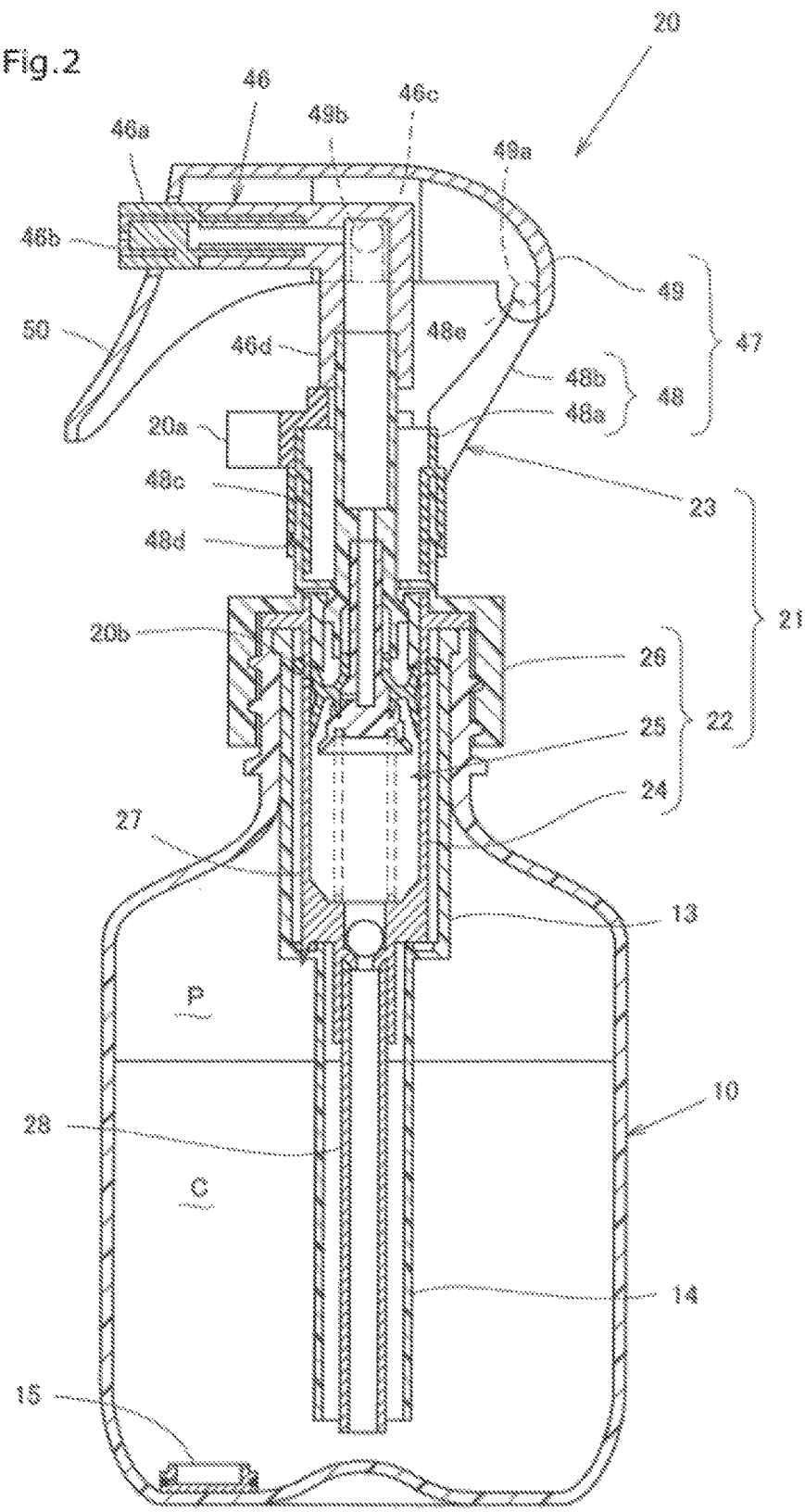
FIG. 2 A cross-sectional view showing one embodiment of the discharge product of the present invention.

A content-accommodating container 10 of FIG. 1 comprises a container body 11 having an opening in the upper end, and a valve accommodating portion 12 which closes the opening thereof, and is fixed to the container body 11. The valve accommodating portion 12 is provided with a tubular housing portion 13 accommodated inside the container body, a tube portion 14 extending downward from the housing portion 13, whose lower end is arranged in the vicinity of the bottom of the container body 11, and a closing portion (first unsealing portion) 15 closing the lower end of the tube portion 14.

A refill content-accommodating product is produced by filling a concentrate and a pressurizing agent in the container body 11 of the content-accommodating container 10.

A discharge product is produced by attaching a removable valve member (discharge device) having a valve mechanism to the refill content-accommodating product, in which the closing portion 15 is unsealed.

The content-accommodating container 10 is provided with the housing portion 13 composed so as to be capable of accommodating the valve housing of the valve member, and further is provided with the closing portion 15 unsealed when the valve member is attached, in the tube portion 14 communicating with a liquid phase of the container body. Therefore, the attaching operation is simple, and the closing portion 15 can be unsealed without decreasing largely the inner pressure, while closing inside the valve accommodating portion with the valve member. Hence, it can be made to be a refill container of contents having a pressure, making it possible to reuse the valve member (discharge device).

The container body 11 is a pressure resistant container made of synthetic resin, in which a bottom portion 11a, a tubular body portion 11b, a taper like shoulder portion 11c, and a tubular neck portion 11d are provided coaxially. The upper end of the neck portion 11d is opened, the inside surface thereof, a step portion 11e to support the upper end of the valve accommodating portion 12 is formed (refer to FIG. 1C). Moreover, in the outer periphery of the neck portion 11d, a male screw 11f for connecting the valve member (discharge device) is formed.

The container body 11 as described above is formed by blow molding, in which the neck portion and mouth portion (a tubular portion above the shoulder portion) of a bottomed tubular parison are held, the lower side than the neck portion of the parison is bi-axially oriented.

The housing portion 13 of the valve accommodating portion 12 and the tube portion 14 thereunder are a tubular body made of synthetic resin integrally formed coaxially. Moreover, the tube portion 14 is reduced in diameter in regard to the housing portion 13.

The housing portion 13 of the valve accommodating portion 12 is a tubular body, in the upper end thereof, a flange portion 13a protruding outward is formed (refer to FIG. 1C). The valve accommodating portion 12 is supported on the container body 11 by contacting the flange portion 13a with the upper surface of the step portion 11e of the container body 11. Further, after or when arranging the flange portion 13a on the step portion 11e, it is preferable to fix airtightly to the container body 11 by welding or adhering. Moreover, in the lower end of the housing portion 13, a step portion 13b protruding inward in the radial direction is formed. In the step portion 13b, a thin wall portion 16 (second unsealing portion) is formed. By fracturing this thin wall portion 16, it serves as a gas introducing passage communicated with the upper space (gas phase A) inside the container body. In the embodiment of FIG. 1, the cylindrical housing portion 13 is disclosed, but, it is not limited particularly as long as it can accommodate the valve housing of the valve member. The tube portion 14 of the valve accommodating portion 12 extends downward from the inside edge portion of the step portion 13b. The lower end thereof is composed so as to communicate with the lower space (the liquid phase L) of the container body 11. Hence, when the closing portion (first unsealing portion) 15 is unsealed, since the pressurizing agent is accommodated inside the container body 11 through the liquid phase L, the pressurizing agent is hard to leak out. This tube 14 portion is particularly provided in the vicinity of the bottom portion 11a of the container body 11. Hence, it acts as a dip tube. However, the lower end of the tube portion 14 is sufficient as long as it communicate with the liquid phase L of the container body 11, when unsealing the closing portion (first unsealing portion) is unsealed.

The closing portion 15 of the valve accommodating portion 12 is that which is, as shown in FIG. 1B, a bottomed tubular body equipped with a connecting portion 15a whose upper end opening is reduced in diameter, and that in which the connecting portion 15a is fitted and attached to the lower end opening of the tube portion 14. Hence, the closing portion 15 can be detached by pressing it downward in regard to the tube portion 14. In the closing portion 15, there is provided a check valve 17 which allows a flow to the container body and blocks a flow from the container body to the inside of the tube portion 14. The check valve 17 comprises a communicating passage 17a formed toward the center hole in the side surface of the closing portion 15, an annular groove 17b provided in the same position with the communicating passage 17a, and an O ring 17c inserted into the annular groove 17b. Stated differently, the communication passage 17a is in a state closed always by the O ring 17c. By flowing a fluid from the inside to the outside of the communicating passage 17a, the O ring 17c is expanded in diameter, and the communicating passage 17a is released.

As the concentrate filled in the content-accommodating container 10, for example, household products used in the space of room interior and car interior containing flavor components, deodorant components, sterilization components, disinfection components etc., household products used in the objects of carpets, curtains, clothes, glasses etc., skin care products containing moisturizing ingredients, astringent ingredients, antiperspirant ingredients, sunscreen ingredients etc., hair care products containing hair styling ingredients, treatment ingredients, cleansing components etc. can be cited.

As the pressurizing agent filled in the content-accommodating container 10, for example, compressed gas such as compressed air, nitrogen gas, carbon dioxide gas, nitrous oxide gas can be cited. If the pressure inside the accommodating container is adjusted so as to be 0.05-0.5 MPa preferably to be 0.1-0.4 MPa by the pressurizing agent, the pressurizing agent effect such as being easy to spray over a wide range is easily obtained.

The method of filling the concentrate and the pressurizing agent in the content-accommodating container 10 can be performed so that the concentrate is filled in the container body 11, after that, the valve accommodating portion 12 is inserted and fixed, at the end, the pressurizing agent is filled from the check valve 17 of the closing portion 15 through the housing portion 13 and the tube portion 14. Moreover, after fixing the valve accommodating portion 12 to the container body 11, the concentrate and the pressurizing agent may be filled through the check valve 17.

As described above, the concentrate is accommodated together with the pressurizing agent, it is possible to prevent the permeation and infiltration of outside air and bacteria into the container body, and to maintain the quality of the concentrate, even if being stored for a long period.

The discharge product 20 of FIG. 2 comprises the content-accommodating container 10 of FIG. 1, a concentrate C and a pressurizing agent P filled inside thereof, and a discharge device 21 attached to the content-accommodating container 10. The discharge device 21 is constituted so that when the content-accommodating container 10 is attached, the closing portion (first unsealing portion) 15 is removed from the tube portion 14. Moreover, the discharge device 21 is provided with an aerosol valve mechanism which discharges (aerosol discharge) the concentrate C by the pressure of the pressurizing agent P, and a valve mechanism 25 equipped with an auxiliary pump mechanism which pressurizes the concentrate by compressing the storing space of the concentrate C when the pressure of the pressurizing agent P becomes weak. Further, the valve mechanism 25 of the discharge device 21 is equipped with an operation switching member 20a for operating the auxiliary pump mechanism.

The discharge device 21 is provided with a valve member 22 equipped with the valve mechanism 25 and an operating member 23 attached to the valve member 22 for operating the valve mechanism 25. Here, the content-accommodating container 10 of FIG. 1 is attached, but the discharge device 21 may be attached to the content-accommodating container not provided with the valve accommodating portion. Stated differently, it can also be made into a discharge product in which the discharge device 21 is attached to the content-accommodating container not provided with the valve accommodating portion. After the use thereof, the content-accommodating container not provided with the valve accommodating portion is discarded, and by attaching the discharge device 21 to the purchased content accommodating product of FIG. 1, the discharge device 21 can be reused.

The valve member 22 comprises a tubular valve housing 24, a valve mechanism 25 housed inside thereof, and a cap 26 which fixes the valve mechanism 25 to the inside of the valve housing 24, and fixes the valve housing 24 to the container body 11.

The valve housing 24 is equipped with a tubular housing body 27 and a dip tube 28 connected to the lower end thereof. The housing body 27 is accommodated in the housing portion 13 of the valve accommodating portion 12, the dip tube 28 is accommodated in the tube portion 14 of the valve accommodating portion 12.

The housing body 27 is, as shown in FIG. 3A, that which is of a cylindrical shape having a bottom portion. In the upper portion of the housing body 27, a flange portion 27a protruding outward in the radial direction is formed, in the center of the bottom portion, a liquid phase communicating hole 27b is formed, and in the upper side surface, a gas phase communicating hole 27c is formed. Moreover, in the lower surface center of the bottom portion, a tubular connecting portion 27d extending downward is formed, in the lower edge surface of the bottom portion, a puncture portion 27e extending downward is formed. Further, above the gas phase communicating hole 27c, an annular groove 27f is formed. And, in the liquid phase communicating hole 27b of the bottom portion, a check valve 29 is provided. In this embodiment, the check valve 29 is provided in the bottom portion coaxially with the liquid phase communicating hole 27b, and it comprises a concave portion 29a of the diameter larger than the liquid phase communicating hole 27b, and a ball valve 29b inserted into the concave portion 29a.

The flange portion 27a is arranged in the upper end of the container body 11 and the valve accommodating portion 12.

The liquid phase communicating hole 27b is a hole for introducing the concentrate C in the container body 11 into inside the housing body 27.

The gas phase communicating hole 27c is a hole which communicates the inside of the housing body 27 with the upper space (the gas phase A) inside the container body 11.

The connecting portion 27d is a portion to connect the later described dip tube 28, and communicates with the liquid phase communicating hole 27b. The puncture portion 27e is constituted so that it can fracture the thin wall portion 16 of the housing portion 13 of the valve accommodating portion 12, when the discharge device 21 is attached to the container body 11 (refer to FIG. 2). In other words, in this embodiment, the puncture portion 27e is the second unsealing means to unseal the thin wall portion 16 (the second unsealing portion).

The annular groove 27f is that which holds an O ring 20b sealing between the valve member 22 and the valve accommodating portion 12. Stated differently, by the insertion of the housing body 27 into the housing portion 13, the O ring 20b is compressed to seal. In addition, the annular groove 27f is provided so that before the later described dip tube 28 contacts the closing portion 25, and before the puncture portion 27e contacts the thin wall portion 16, the O ring 20b contacts the inner surface of the housing portion 13 and is compressed. Accordingly, after sealing is formed by the O ring 20b, the first unsealing portion and the second unsealing portion are unsealed, the contents are harder to leak out.

Returning to FIG. 2, the dip tube 28 is that which is connected to the connecting portion 27d of the housing body 27, extends to the vicinity of the lower end of the container body 11, and sucks up the concentrate C in the container body 11 toward inside the housing body 24. Moreover, the dip tube 28 is constituted so that, when the discharge device 21 is attached to the container body 11, the lower end thereof is positioned lower than the lower end of the tube portion 14. In other words, when the discharge device 21 (the valve member 22) is attached to the container body 11, the lower end of the dip tube 28 pushes the closing portion 15 downward to remove the closing portion 15 from the tube portion 14. Hence, in this embodiment, the dip tube 28 is the first unsealing means to unseal the closing portion (first unsealing portion).

The valve mechanism 25 is, as shown in FIG. 3B, provided with a stem 31 accommodated in the housing body 27 of the valve housing 24 to be freely movable vertically, a piston 32 sliding on the inner periphery of the housing body 27 in which the stem 31 is inserted, and a spring 33 which energizes the stem 31 upward. This valve mechanism 25 is a valve mechanism which performs aerosol discharge, and is that in which an auxiliary pump mechanism is provided, which compensates the discharge power of the concentrate C, when the pressure of the pressurizing agent becomes weak.

The stem 31 comprises an internal stem 36 in which a stem hole 36a is provided, and an external stem 37 attached above the inner stem 26, protruding upward from the container body 11 (refer to FIG. 2).

The internal stem 36 presents a cup shape facing downward as shown in FIG. 3C, and has a large diameter cup shaped portion 38 with which the upper end of the spring 33 is engagingly stopped, and a small rod like portion 39 protruding upward from the upper surface center of the cup shaped portion 38.

In the circumference of the root of the rod like portion 39 in the upper surface of the cup shaped portion 38, an annular upper groove 38a with which the lower end of a later described inside sliding portion 32a of the piston 32 engages is formed. In the lower surface of the cup shaped portion 38, an annular lower groove 38b to accept the spring 33 is formed.

In the rod like portion 39, a tubular columnar portion 39a in the side surface of which a stem hole 36a communicating with the center hole is formed, a tubular oblique portion 39b reduced in diameter upward from the upper end thereof, and a tubular small diameter portion 39c formed upper than the upper end of the oblique portion 39 b are coaxially formed.

The external stem 37 is a portion where a later described operating member is attached. The external stem 37 has a tubular skirt portion 37a composed so as to surround the rod like portion 39 as shown in FIG. 3D, and a tubular portion 37b reduced in diameter extending upward from the skirt portion 37a. The outer diameter of the skirt portion 37a is of almost same diameter or somewhat smaller diameter than the cup shaped portion 38, and the inner diameter is composed so that a gap is formed across the outer periphery of the rod like portion 39.

The tubular portion 37b is connected to the internal stem 36 by accepting a small tube portion 39c of the rod like portion 39 with the lower end thereof. The upper portion of the tubular portion 37b protrudes upward from the container body 11, and to the upper portion of the tubular portion 37b, the operating member is attached (refer to FIG. 2).

The piston 32 presents, as shown in FIG. 3E, a double tubular shape, and comprises an inside sliding portion 32a sliding on the outer surface of the internal stem 36, an outside sliding portion 32b sliding on the inner surface of the housing body 27 and an annular connecting ring 32c connecting those. The connecting ring 32c is that which connects the inside sliding portion 32a and the vicinity of the center of the outside sliding portion 32b. This piston 32 partitions the inside of the housing body 27 into two independent spaces (a lower space S1, an upper space S2) (refer to FIG. 3B). And, the lower space S1 serves as a space to store the concentrate C. In addition, being described later, the upper space S2 becomes in a state communicated with outside air when the stem 31 operates. Hence, when the inside of the container body becomes negative pressure by the piston whose position is restored by the spring, outside air is introduced through the upper space S2, the gas phase communicating hole 27c, and the gas phase introducing portion (the fractured thin wall portion 16).

The inside sliding portion 32a is that which opens and closes the stem hole 36a of the internal stem 36, and moves vertically between the internal stem 36 and the external stem 37 (refer to FIG. 3B). Moreover, the lower end of the inside sliding portion 32a receives the groove 38a of the cup shaped potion 38 of the internal stem 36 as described above, the piston 32 is energized upward.

The outside sliding portion 32b is that which opens and closes the gas phase communicating hole 27c (refer to FIG. 3B). The connecting ring 32c is a portion to receive the lower end of the skirt portion 37a of the external stem 37. As later described, the connecting ring 32c receives the downward pressure from the external stem 37, and lowers the piston 32 downward. Such piston 32 is made from elastic materials such as synthetic resin, silicon rubber, and synthetic rubber.

The spring 33 is arranged so as to be compressed between the bottom portion of the housing body 27 of the valve housing 24 and the lower groove 38b of the cup shaped portion 38 of the internal stem 36 of the stem 31. Thereby the stem 31 is energized upward.

The cap 26 comprises, as shown in FIG. 3B, a cap body 41, having an upper bottom 41a, and a tubular attaching portion 42 protruding upward from the upper surface center thereof. The attaching portion 42 is provided so as to penetrate the upper bottom 41a of the cap body 41. In the inside surface of the cap body 41, a female screw 41b screwing with a male screw 11f of the container body 11 is formed. In the inner surface of the lower portion of the attaching portion 42, a ring like cover portion 42a protruding inward in the radial direction is formed. Moreover, in the outer periphery surface of the attaching portion 42, an engaging protrusion 42b is formed.

Between the cap 26 and the housing 24, a presser member 43 and a seal material 44 are provided. In detail, the presser member 43 has a tubular spacer portion 43a inserted so as to make nearly close contact with the inner periphery wall of the housing body 27, an annular outer seal piece 43b extending outward in the radial direction from the upper end of the spacer portion 43a, and an inner seal piece 43c extending inward in the radial direction from the upper end of the spacer portion 43a. The lower end of the spacer 43a contacts with the upper end of the piston 32 and positions the piston 32 in the initial state (lock position). The lower surface of the outer seal piece 43b contacts the upper end of the housing body 27, and the upper surface thereof is connected with the cover portion 42a through the seal material 44. The inner seal piece 43c suppresses the upper surface of the skirt portion 37a of the external stem 37, when the stem 31 is in an end position of ascending and confines the jumping out upward of the stem 31. The seal material 44 presents an approximately L shape in cross section from the upper surface of the outer seal piece 43b to the inner end of the inner seal piece 43c. This seal material 44 is pressed by the lower surface thereof by the screwing of the cap 26, and seals between the presser member 43 and the cap 26 and between the presser member 43 and the external stem 37.

Hence, when the stem 31 is in a locked state (the ascending end of the initial state), it contacts the upper surface of the skirt portion 37a of the external stem 37 and performs sealing, and when the stem 31 is pushed down, it makes the upper space S2 and outside air being capable of communicating.

The valve member constituted as described above is fixed to the container body 11 so that the housing body 27 and the dip tube 28 are inserted into the housing portion 13 and the tube portion 14 of the valve accommodating portion respectively, the female screw 41b of the cap 26 is screwed to the male screw 11f of the container body 11 of the content-accommodating container. In addition, before being completely attached to the container body 11, the O ring 20b of the housing body 27 is compressed across the inner surface of the housing portion 13 of the valve accommodating portion 12, making the inside of the housing portion 13 to be in an airtight state. And, almost at the same time, or when the cap 26 is turned, by the lower end of the dip tube 28, the closing portion 15 is unsealed introducing the concentrate C into inside the dip tube 28, moreover, by the puncture portion 27e of the valve housing portion 24, the thin wall portion 16 is unsealed, forming the gas introducing passage. Since, as described above, since it is possible to seal inside the valve accommodating portion 12 (the housing portion and the tube portion 14) before the first unsealing portion is unsealed by the first unsealing means and the second unsealing portion is unsealed by the second unsealing means, the concentrate C and the pressurizing agent P never leak out to the exterior.

Moreover, unsealing the thin wall portion 16 by puncture portion 27e of the valve housing portion 24 to form the gas introducing passage, the pressurizing agent P is introduced into the space between the housing portion 13 and the valve housing 24, making the undiluted solution C do not enter between the housing portion 13 and the valve housing 24. And, it is possible to induce the surely pressurized concentrate C into the dip tube 28. Further, due to the repetition of use, the pressure inside the container body 11 becomes low, deteriorating the discharge state of the concentrate C, if the auxiliary pump mechanism is operated, by the discharge of the concentrate C, the inside the container body 11 becomes in a reduced pressure state, but outside air is introduced in the container body through the gas phase communication hole 27c and the gas introducing passage (the thin wall portion 16 and the puncture portion 27e), the concentrate C can be introduced into the inside of the housing body 27.

Next, the operating state of the valve mechanism 25 is described. The valve mechanism 25 operates as shown in FIG. 4A-4C by lowering the stem 31. The valve mechanism 25 is that which presents an aerosol discharge state initially, and switches to a pump discharge state, when the stem 31 is lowered more than a certain amount.

In detail, the operating member 23 is operated from the initial state of FIG. 4A, the stem 31 is moved as large as the moving amount H1 as shown in FIG. 4B. Thereby, the internal stem 36 and the external stem 37 lower integrally. At this moment, the rod like portion 39 of the internal stem 36 slides on the inner surface of the inside sliding portion 32a of the piston 32, the stem hole 36a is released from the inside sliding portion 32a of the piston 32. Meanwhile since the piston 32 does not operate, the volume of the lower space S1 is maintained. Thereby, concentrate C stored in the lower space S1 from the dip tube 28 is pressurized by the pressurizing agent P, passes through the stem hole 36a, and is supplied to the operating member 23 through the internal stem 36 and the external stem 37. As described above, by moving the stem 31 as large as the moving amount H1, the concentrate C can be discharged as an aerosol valve.

On the other hand, the stem 31 is further moved as large as the moving amount H2, as shown in FIG. 4C, the lower end of the skirt portion 37*a* of the external stem 37 contacts the connecting ring 32*c* of the piston 32, the lower end of the skirt portion 37*a* lowers the piston 32. Thereby, the lower space S1 is compressed, the concentrate C in the lower space S1 is discharged by the applied compressing force. In other words, the stem 31 and the piston 32 present the auxiliary pump mechanism.

By the lowering of the piston 32 sliding on the inner surface of the housing body 27, the gas phase communicating hole 27*c* is released from the outside sliding portion 32*b*. Stated differently, the upper space S2 upper than the piston 32 and the inside of the container body 11 communicate through the gas phase communicating hole 27*c* of the housing body and the gas introducing passage formed in the housing portion 13. Thereby, the upper space S2 and the lower space S1 of the housing body 27 becomes of the same pressure instantly. Thereby, the operating force to move the piston 32 downward (the downward operating force of the stem 31) decreases, the operation activity of the auxiliary pump mechanism becomes easy. And, since the check valve 29 is provided in the liquid phase communicating hole 27*b*, the concentrate C in the lower space S1 never flows back to inside the container body 11, being pressurized by the piston 32, sent to the operating member 23 from the stem hole 36*a*, and is discharged outside.

When the operation of the operating member 23 is stopped, the stem 31 and the piston 32 move upward by the spring force of the spring 33, at this moment, outside air is introduced into inside the container body 11 through the gas phase communicating hole 27*c* and the gas introducing passage, the concentrate C is introduced into inside the lower space S1 of the housing body 27.

In addition, after the operation, by the ascending of the piston 32, the gas phase communicating hole 27*c* is plugged by the outside sliding portion 32*b*. However, the upper space S2 and outside air is communicated as described above, when the stem 31 moves, the upper space S2 is gradually depressurized. In other words, after the operation, the pressure of the upper space S2 becomes lower than that of the lower space S1, the restoring of the piston 32 to the initial state by the spring 33 is not disturbed.

Meanwhile, by operating the piston 32 up to the state of FIG. 4C more than once, the pressurizing agent in the container body 11 can be discharged into the atmosphere through the upper space S2. After the pressurizing agent P in the container body 11 is discharged, the stem 31 and the piston 32 serve as a pure pump valve to discharge the concentrate C. Whether the pure pump valve discharge state is presented or not can be properly set by the initial condition of the concentrate C and the pressurizing agent P filled in the content-accommodating container 10 and the sealing force of the seal material 44.

Returning to FIG. 2, the operating member 23 comprises a spray nozzle 46 attached to the stem 31 and an operating member 47 attached to the cap 26. The spray nozzle 46 is an L-letter shaped tubular body and is provided with a nozzle hole member 46*a*. In the tip of the nozzle hole member 46*a*, a nozzle tip 46*b* is provided, constituting a mechanical breakup mechanism. Moreover, in the upper both sides of the spray nozzle 46, a turning shaft 46*c* is provided. In the lower end of the spray nozzle 46, a stem engaging portion 46*d* to be connected with the stem 31 is formed. Further, in the stem engaging portion 46*d*, a lock groove 46*e* extending upward from the lower end is formed (refer to FIG. 5B, C).

The operating portion 47 comprises a lever supporting portion 48 attached to the attaching portion 42 of the cap 26, and a lever 49 mounted on the lever supporting portion 48 freely rotatably.

The lever supporting portion 48 is equipped with a tubular body 48*a* and a supporting arm 48*b* protruding from the side wall of the body thereof. In the lower end of the body 48*a*, an annular groove 48*c* to accept the attaching portion 42 of the cap 26 is formed. Further, in the inner surface of the annular groove 48*c*, an engaging groove 48*d* to accept the engaging protrusion 42*b* of the attaching portion 42 is formed. As described above, by inserting the attaching portion 42 into the annular groove 48*c*, the cap 26 and the operating portion 47 are connected. In the upper end of an arm 48*b*, a turning shaft 48*e* is provided, the lever 49 is attached freely turnably. The lever 49 is that which extends curvedly to the front end from the back end so as to cover the later described spray nozzle 46. In the tip of the lever 49, a trigger 50 for the pulling operation with the finger is provided extending obliquely downward in front. In the back end of the lever 49, a bearing 49*a* to receive the turning shaft of the arm 48*b* is formed. Moreover, in the lower surface center of the lever 49, a bearing 49*b* to receive the turning shaft 46*c* of the spray nozzle 46 is formed.

Being constituted as described above, by pulling the trigger 50 of the operation member 23, the lever 49 turns, centering around the back end, and presses the spray nozzle 46 downward through the bearing 49*b*.

In this discharge device 20, an operation switching member 20*a* is provided in the valve mechanism 25 for preventing malfunction of the auxiliary pump mechanism.

The operation switching member 20*a* is a tubular body, having a knob portion 51 protruding outward in the radial direction from vicinity of the center of the side surface, having an inside flange portion 52 protruding inward in the radial direction in the upper end, and having a lock portion 53 protruding upward from the center tip of the inside flange portion 52.

This operation switching member 20*a* is, as shown in FIG. 5, that which controls the downward moving distance of spray nozzle 46 of the operating member 23. Stated differently, as shown in FIG. 5B, it is composed so that when the lock portion 53 is in the same position as the lower end of the spray nozzle 46, the downward movement of the spray nozzle 46 is disturbed, making the stem 31 not to be moved even if the operating member 23 is operated. Meanwhile, as shown in FIG. 5C, by rotating the operation switching member 20*a* at an angle of 90 degrees, and moving the lock portion 53 up to the position of the lock groove 46*e* of the spray nozzle 46, it becomes possible for the spray nozzle 46 to be moved downward (the moving amount H1), reaching the state of the aerosol discharge. In addition, since the height of the lock groove 46*e* is substantially same as the height of the lock portion 53, it is composed so that the lower end of the spray nozzle 46 cannot move downward lower than the inside flange portion 52 of the operation switching member 20*a*. As described above, when the operation switching member 20*a* is attached, the moving amount of the stem 31 (the spray nozzle 46) is regulated to be in the aerosol discharge state (the moving amount H1). Meanwhile, when operating the auxiliary pump mechanism, the operation switching member 20*a* is removed. Thereby, it is possible to prevent malfunction of the switching because of users.

The content-accommodating container 10 of FIG. 1 can be used in other than the discharge device 21 equipped with the valve mechanism in which the aerosol discharge state and the pump discharge state as shown in FIG. 2 can be switched. For example, the discharge product 60 of FIG. 6A is that in which a discharge device 61 equipped with the aerosol valve mechanism is attached, the discharge product 70 of FIG. 6B is that in which a discharge device 71 equipped with the pump valve mechanism is attached. In addition, also the discharge device 61 of FIG. 6A and the discharge device 71 of FIG. 6B, in the same way as the discharge device 21 of FIG. 2, can be made into a discharge product attached to a content-accommodating container not equipped with the valve accommodating portion.

The discharge device 61 of FIG. 6A comprises a valve member 62 having and aerosol valve mechanism, and an operating member 63 attached to the valve member. The valve member 62 is provided with a tubular valve housing 64, an aerosol valve mechanism 65 housed inside thereof, and a cap 66 which fixes the valve mechanism 65 to the inside of the valve housing 64 and fixes the valve housing 64 to the container body 11.

The valve housing 64 is provided with a tubular housing body 67, and the dip tube 28 connected to the lower end thereof. The housing body 67 is accommodated inside the housing portion 13 of the valve accommodating portion 12, the dip tube 28 is accommodated inside the tube portion 14 of the valve accommodating portion 12. The dip tube 28 is substantially same as the dip tube 28 of FIG. 1.

The housing body 67 is that which is of a cylindrical shape having a bottom portion, in the upper portion thereof, a flange portion 67a protruding outward in the radial direction is formed, in the center of the bottom portion, a liquid phase communicating hole 67b is formed. Moreover, in the inner edge of the flange portion 67a, a step portion 67c reduced in diameter facing downward is formed. Further, in the center of the lower surface, a tubular connecting portion 67d extending downward is formed. In the side surface of the connecting portion 67d, an annular seal material 67e is provided. This housing body 67 has not the puncture portion and the side surface connecting hole.

The flange portion 67a is arranged on the upper end of the container body 11 and the valve accommodating portion 12 sandwiching the annular seal material 60a. The seal material 60a exerts sealing action by being compressed in the vertical direction along with the rotation of the cap when the valve member is attached. Since being provided with such a seal structure as described above, it follows that the sealing of the valve accommodating portion 22 by the valve member 62 and the unsealing of the closing portion 15 are performed almost at the same time, making it possible to prevent the pressurizing agent P from leaking out to the exterior.

The liquid phase communicating hole 67b is a hole to introduce the concentrate C inside the container body 67.

The step portion 67c holds the stem rubber of a later described aerosol valve mechanism 65.

The connecting portion 67d is a portion to connect the dip tube 28, and communicates with the liquid phase communicating hole 67b.

The seal material 67e performs sealing between the connecting portion 67d and the tube portion 14.

The aerosol valve mechanism 65 is substantially same as publicly known aerosol valve mechanisms, and comprises a stem 65a, a stem rubber 65b closing the stem hole thereof, and a spring 65c energizing always the stem 65a upward. The stem 65a and the stem rubber 65b are fixed inside the housing body 67 by the cap 66.

The cap 66 is a tubular body having an upper bottom 66a. In the upper bottom 66a, a center hole is formed. By the upper bottom 66a, the stem rubber 65b is held, and the center hole gives passage to the stem 65a. In the inside surface of the cap 66, a female screw 66b screwing with the male screw 11f of the container body 11 is formed. Further, above the inside surface of the cap 66 (upper than the female screw 66b), an annular engaging protrusion 66c which sandwiches the flange portion 67a of the housing body 67 across the upper bottom 66a is formed. Thereby, the housing body 67 and the cap 66 can be integrally operated.

The operating member 63 has a stem engaging portion 63a in the lower end thereof, has a discharge portion 63b in the side surface thereof, and has an internal passage 63c inside thereof communicating the stem engaging portion 63a and the discharge portion 63b. In the discharge portion 63b, a nozzle tip 63d constituting the mechanical breakup mechanism is provided. This operating member 63 is that which is of a push button type which can push down the stem by being pushed downward from the upper surface. As the operating member 63, a trigger-type operating member such as shown in FIG. 1 may be used, the operating member 63 is not particularly limited as long as it can perform the push down operation of the stem.

In the case that a discharge device for aerosol valve only is attached such as the discharge product 60, adjusting the pressuring agent by a compressed gas according to the volume of the container body, it becomes possible to maintain the discharge state of the concentrate to the last. Moreover, as the pressurizing agent, liquid gas may be used.

On the other hand, the discharge device 71 of FIG. 6B is provided with a valve member 72 having a pump valve mechanism and the operating member 63 attached to the valve member 72. The valve member 72 is provided with a tubular valve housing 74, a pump valve mechanism 75 housed inside thereof, and a cap 76 which fixes the valve mechanism 75 to the inside of the valve housing 74 and fixes the valve housing 74 to the container body 11. The operating member 63 is that which is of a push button type same as that shown in FIG. 6A.

The valve housing 74 is that which is same as the valve housing 24 of FIG. 1, and is provided with the housing body 27 and the dip tube 28. In addition, in the lower surface of the flange portion 27a of the housing body 27, an annular seal material 70a is provided. In this seal structure also, it follows that the sealing of the valve accommodating portion 22 by the valve member 72, the unsealing of the closed portion 15, and the unsealing of the thin wall portion 16 by the puncture portion 27e are performed almost at the same time, it is possible to prevent the concentrate C and the pressurizing agent P from leaking out to the exterior.

The pump valve mechanism 75 is a valve mechanism which pressurizes inside the valve housing 74 or inside the container body 11 by pushing down the stem and discharges the content by the pressure thereof. In this embodiment, a pump mechanism is adopted, in which the content supplied to inside the closed space S3 (pressure chamber) provided inside the valve housing 74 is pressurized by contracting the closed space, and is discharged. However, another pump mechanism such as a pump mechanism in which inside the container body is directly pressurized to discharge the contents may be adopted. In addition, since the content accommodating container 10 of the discharge product 70 has an inner pressure (the concentrate C and the pressurizing agent P), the discharge of the discharge product 70 is not the discharge by the pure pump valve, but depending on the content of the filled pressurizing agent P, the pressurizing agent P exerts an auxiliary role.

The valve pump mechanism 75 is provided with a tubular stem 75a which communicate the housing body 27 with outside air, being accommodated inside the housing body 27, and being movable freely in the axial direction of the housing body 27, a valve member 75b receiving the stem 75a, and being movable freely in the axial direction of the housing body, a piston 75c provided so as to be freely movable between the stem 75a and the valve member 75b, and to be slidable on the inner periphery of the housing body 27, a spring 75d provided between the lower end of the valve member 75b and the bottom portion of the housing body 27, and a check valve 75e which allows the flow from inside the container body 11 to inside the housing body 27 and blocks the flow from inside the housing body 27 to the container body 11. A closed space (pressure chamber) S3 being inside the housing body 27 of the valve pump mechanism 75 is formed by the piston 75c and the check valve 75e.

And, by the pushing down of the stem 75a, the valve member 75 is pushed down to compress the closed space, the piston 75c moves upward between the stem 75a and the valve member 75b, the concentrate is discharged outside from the stem 75a passing through between the stem 75a and the valve member 75b.

In addition, in the case that a discharge device for a pump valve only is attached, by setting the pressure of the pressurizing agent according to the volume of the container body, although being the discharge device for pump valve only, the pressure reduction inside the container body due to the discharge of the concentrate can be canceled out by the pressurizing agent. Hence, even if the gas phase communicating hole 27c and the gas introducing hole (the puncture portion 27e and the thin wall portion 16) of FIG. 6B are not provided, it becomes possible to discharge to the last.

In the content-discharge container 80 of FIG. 7A, the closing portion (the first unsealing portion) is provided in the inside, not in the lower end of the valve accommodating portion 82. Moreover, instead of providing the check valve in the closing portion, a slit 81a extending vertically in the inner surface of the container body 81 for filling a pressurizing agent is formed. In detail, it comprises a container body 81 having an opening in the upper end and a valve accommodating portion 82 which closes the opening, and is fixed to the container body 81. The valve accommodating portion 82 is provided with the tubular housing portion 13 accommodated in the container body, a tube portion 14 extending downward from the housing portion 13, the lower end of which is arranged in the vicinity of the bottom of the container body 11, and a closing portion (first unsealing portion) 83 closing the upper end of the tube portion 14. Moreover, a protection cover 84 is provided so as to cover the container body 81 and the valve accommodating portion 82. Moreover, the housing portion 13 and the tube portion 14 of the valve accommodating portion 82 are substantially same as the housing portion 13 and the tube portion 14 of FIG. 1.

This content-accommodating container 80 also becomes a refill content accommodating product by filling a concentrate and a pressurizing agent same as the content-accommodating container 10 of FIG. 1. And, by attaching the discharge device equipped with the valve member to the refill content-accommodating product, it becomes a discharge product.

The content-accommodating container 80 also is, same as the content-accommodating container 10 of FIG. 1, equipped with the housing portion 13 composed so as to accommodate the valve housing of the discharge device, and further, a closing portion 83 unsealed when the valve member is attached. Hence, it can be made to be a refill container of contents having a pressure, the discharge device can be reused.

The container body 81 is that in which the slit 81a extending downward vertically from the upper end in the inner surface of the neck portion is provided. Another composition is substantially same as the container body of FIG. 1. This slit 81a serves as a passage for filling a pressurizing agent as later described.

The closing portion 83 is a planar portion provided integrally in the upper end of the tube portion 14. And, the closing portion 83 and the tube portion 14 are connected through an annular thin wall-like fracture portion 83a. Being composed as described above, if the closing portion 83 is strongly pressed by the first unsealing means of the discharge device, the fracture portion 83a is broken, and the closing portion 83 is unsealed. The protection cover 84 is a tubular body having an upper bottom, and is that which prevents foreign materials from entering inside the housing portion 13 during storage or at point of sales.

The protection cover 84 as described above may be used in another content-accommodating container of the present invention of content-accommodating container 10 etc. of FIG. 1.

In this content-accommodating container 80 also, the concentrate and the pressurizing agent same as the content-accommodating container 10 of FIG. 1 are filled.

In addition, the method to fill the concentrate and the pressurizing agent into the content-accommodating container 80 is to fill the concentrate into the container body 81. After that, just before fixing the valve accommodating portion 82 to the container body 81, the pressurizing agent is filled from between the valve accommodating portion 82 and the container body 81 through the slit 81a of the container body 81. At the same time as the filling of the pressurizing agent, the valve accommodating portion 82 is attached to the container body 81, the valve accommodating portion 82 is fixed by welding etc.

This content-accommodating container 80 also can protect the concentrate and the pressurizing agent from outside air, the quality of the concentrate can be maintained, even if being stored for a long period.

The content-accommodating container 85 of FIG. 7B is that which is provided with a ring like holding cover 86 made of metal, which fixes the container body 81 and the valve accommodating portion 82. Moreover, in the upper end of the container body 81, an upper end flange 81b is formed. The end portion of the protection cover 86 is swaged to the upper end flange 81b. Another composition is substantially same as the content-accommodating container 80 of FIG. 7A.

Figure 8:
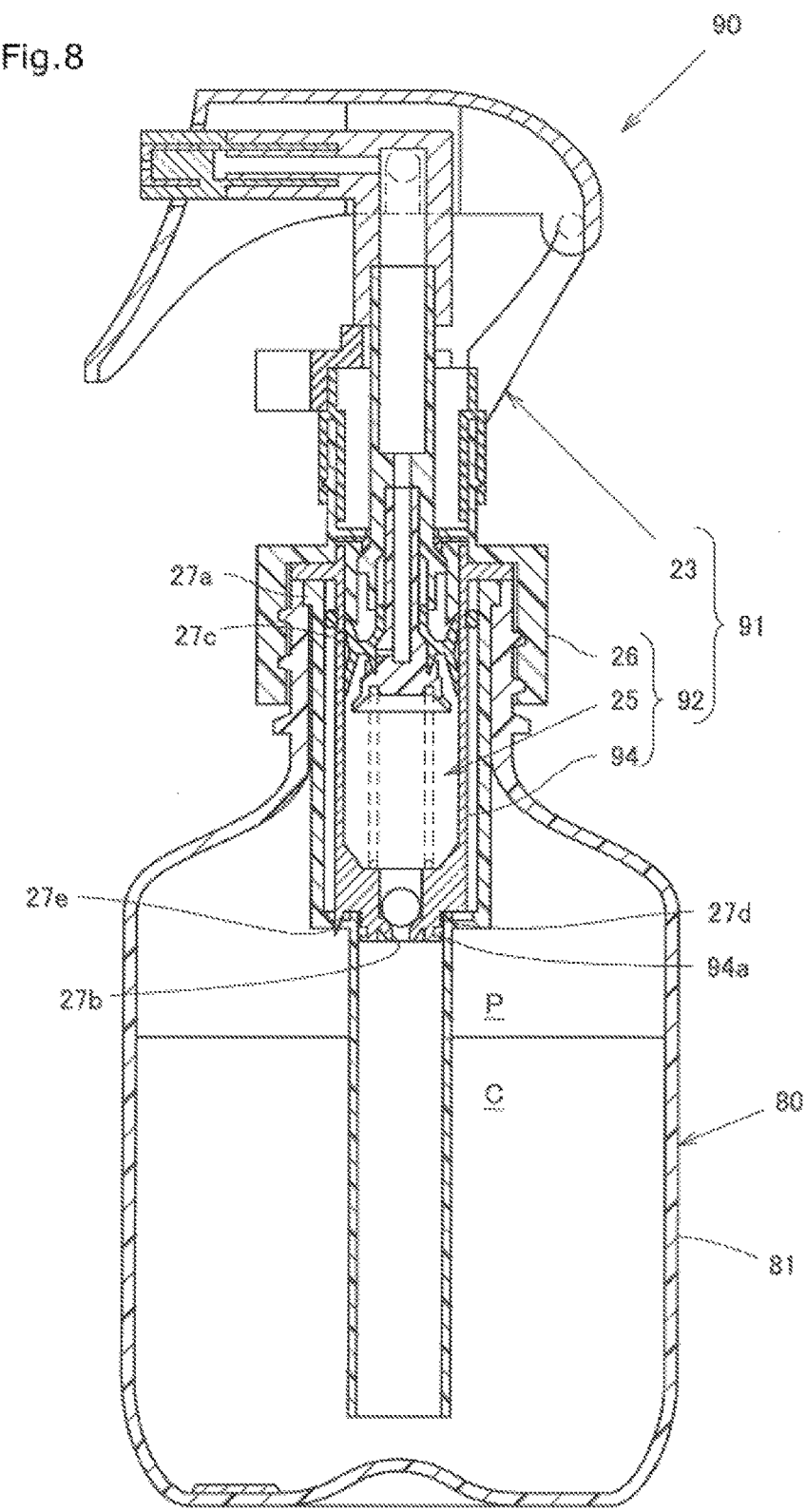
FIG. 8 A cross-sectional view showing further another embodiment of the discharge product of the preset invention.

The discharge product 90 of FIG. 8 comprises the content-accommodating container 80 of FIG. 7A, the concentrate C and the pressurizing agent P, and a discharge device 91 attached to container body 81 of the content-accommodating container 80.

The discharge device 91 is constituted so that, when the content-accommodating container 80 is attached, the closing portion 83 of the content-accommodating container 80 is fractured from the tube portion 14, and that the gas phase introducing passage is formed by breaking through the thin wall portion 16 of the housing portion 13. The discharge device 91 is a valve mechanism which discharges (aerosol discharge) the concentrate C by the pressure of the pressurizing agent P, and is equipped with a valve mechanism in which an auxiliary pump mechanism to compress the concentrate C by operation when the pressure of the pressurizing agent becomes weak. This discharge device 91 is equipped with the operation switching member 20*a* same as the discharge device 21 of FIG. 2.

The discharge device 91 is equipped with a valve member 92 having the valve mechanism and the operating member 23 attached to the valve member 92. The valve member 92 is equipped with a tubular valve housing 94, the valve mechanism 25 housed inside thereof, and the cap 26 which fixes the valve mechanism 25 to the inside of the valve housing 94 and fixes the valve housing 94 to the container body 81.

The operating member 23 is that which is substantially same as the operating member 23 of FIG. 1. Moreover, the valve mechanism 25 of the valve member 92 and the cap 26 are those which are substantially same as the valve mechanism 25 and the cap 26 of FIG. 1.

In addition, the discharge device 91 also can be made into a discharge product attached to the content-accommodating container not equipped with the valve accommodating portion.

A valve housing 94 is not equipped with the dip tube, and is that which is substantially same as the valve housing 24 other than that an annular seal material 94*a* is provided in the outer periphery surface of the connecting portion 27*d*. Stated differently, the valve housing 94 is equipped with the flange portion 27*a*, the liquid phase communicating hole 27*b*, the gas phase communicating hole 27*c*, the connecting portion 27*d*, the puncture portion 27*e*, and the check valve 29.

In this discharge product 90, the discharge device 91 is used, but any of the discharge device 21 (aerosol valve with the auxiliary pump mechanism) of FIG. 1, the discharge device 61 (aerosol valve) of FIG. 6A, and the discharge device 71 (pump valve) of FIG. 6B can be used.

Figure 9:
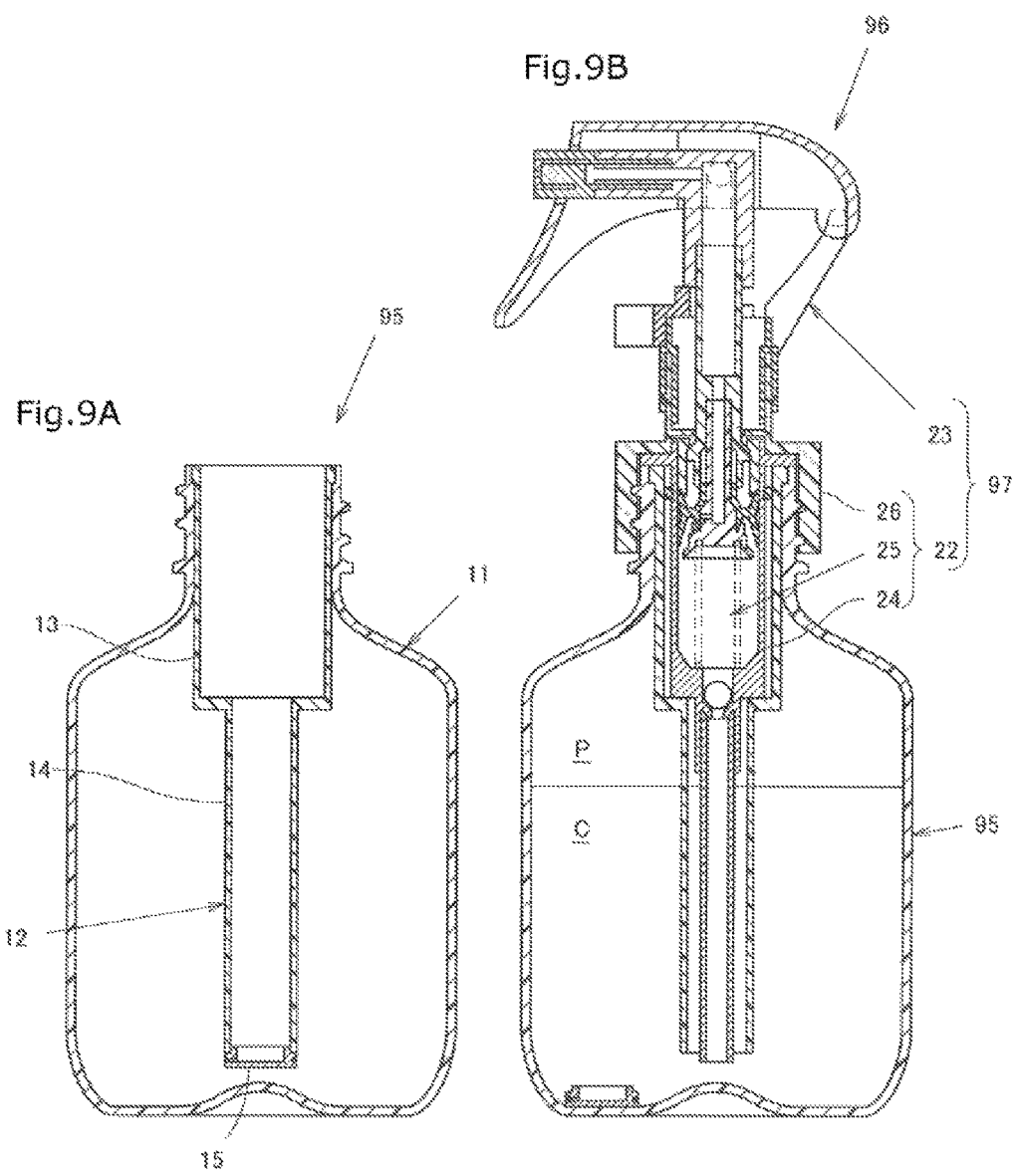
FIG. 9A is a cross-sectional view showing further another embodiment of the content-accommodating container of the preset invention.
FIG. 9B is a cross-sectional view showing further another embodiment of the discharge product of the preset invention.

The content-accommodating container 95 of FIG. 9A is that which is substantially same as the content-accommodating container 10 of FIG. 1 excepting the point that it is not equipped with the thin wall portion 16. The discharge product 96 of FIG. 9B comprises the content-accommodating container 95 of FIG. 9A, the concentrate C and the pressurizing agent P filled inside thereof, and a discharge device 97 attached to the container body 11 of the content-accommodating container 95. The discharge device 97 is that which is substantially same as the discharge device 21 of FIG. 2, excepting the point that it is not equipped with the gas phase communicating hole 27*c* and the puncture portion 27*e* of the housing body 27.

This discharge product 96 also is that which, same as the discharge product 20 of FIG. 2, discharges the concentrate C in an aerosol state, and compensates by the auxiliary pump mechanism, when the pressure of the pressurizing agent becomes weak. However, it is not equipped with the gas phase communicating hole and the gas introducing hole (the thin wall portion fractured by the puncture portion), different to the discharge device of FIG. 2, the pressurizing agent remains inside the container body 11, even if the piston 32 is lowered. Hence, even if the stem 31 is pushed down more than once, the pressurizing agent P never escapes, making it possible to continue a similar discharge state.

Figure 10:
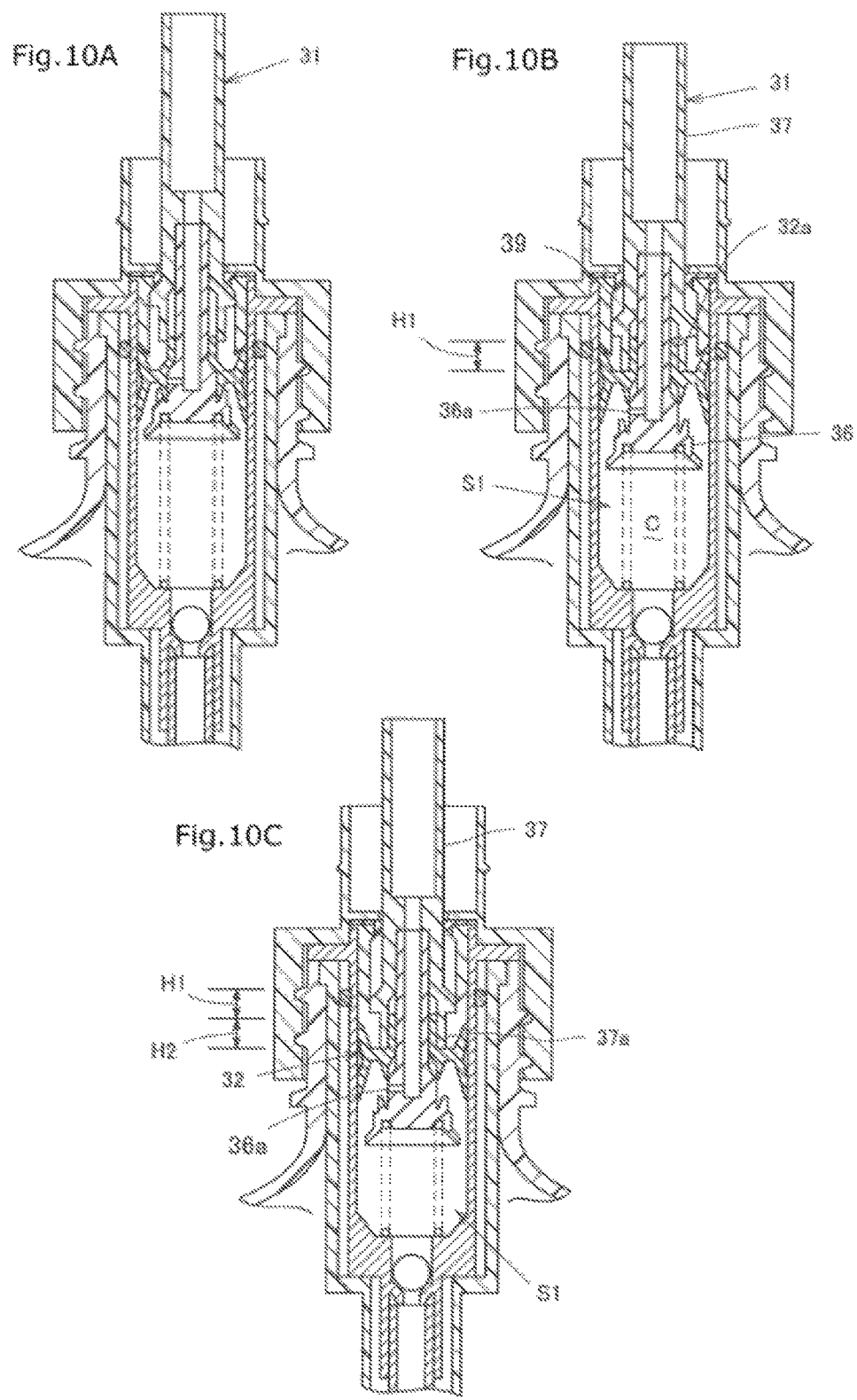
FIG. 10A-C are cross-sectional views showing the stopped state, the aerosol discharging state, and the pump discharging state of the valve mechanism of the discharge product of FIG. 9B respectively.

In detail, the operating member 23 is operated from the state of FIG. 10A, and the stem 31 is moved as large as the moving amount H1 as FIG. 10B. Thereby, the internal stem 36 and the external stem 37 lower integrally. In this moment, the rod like portion 39 of the internal stem 36 slides on the inner surface of the inside sliding portion 32*a* of the piston 32, the stem hole 31*a* is released from the inside sliding portion 32*a* of the piston 32. Thereby, the concentrate C stored in the lower space S1 passes through the stem hole 36*a* which is pressurized by the pressurizing agent P, and supplied to the operating member 23 through the internal stem 36 and the external stem 37. As described above, by moving the stem 31 as large as the moving amount of H1, it is possible to discharge the concentrate C as an aerosol valve.

Meanwhile, when the discharge by the aerosol discharge has become weak, if the stem 31 is lowered as large as the moving amount H2, as shown in FIG. 10C, the lower end of the skirt portion 37*a* of the external stem 37 contacts the connecting ring 32*c* of the piston 32, and the lower end of the skirt portion 37*a* lowers the piston 32. Thereby, the lower space S1 of the housing body 27 is compressed by the piston 32, the concentrate in the lower space S1 is discharged by the applied compressing force thereof. In other words, the stem 31 and the piston 32 present the auxiliary pump mechanism.

Figure 11:
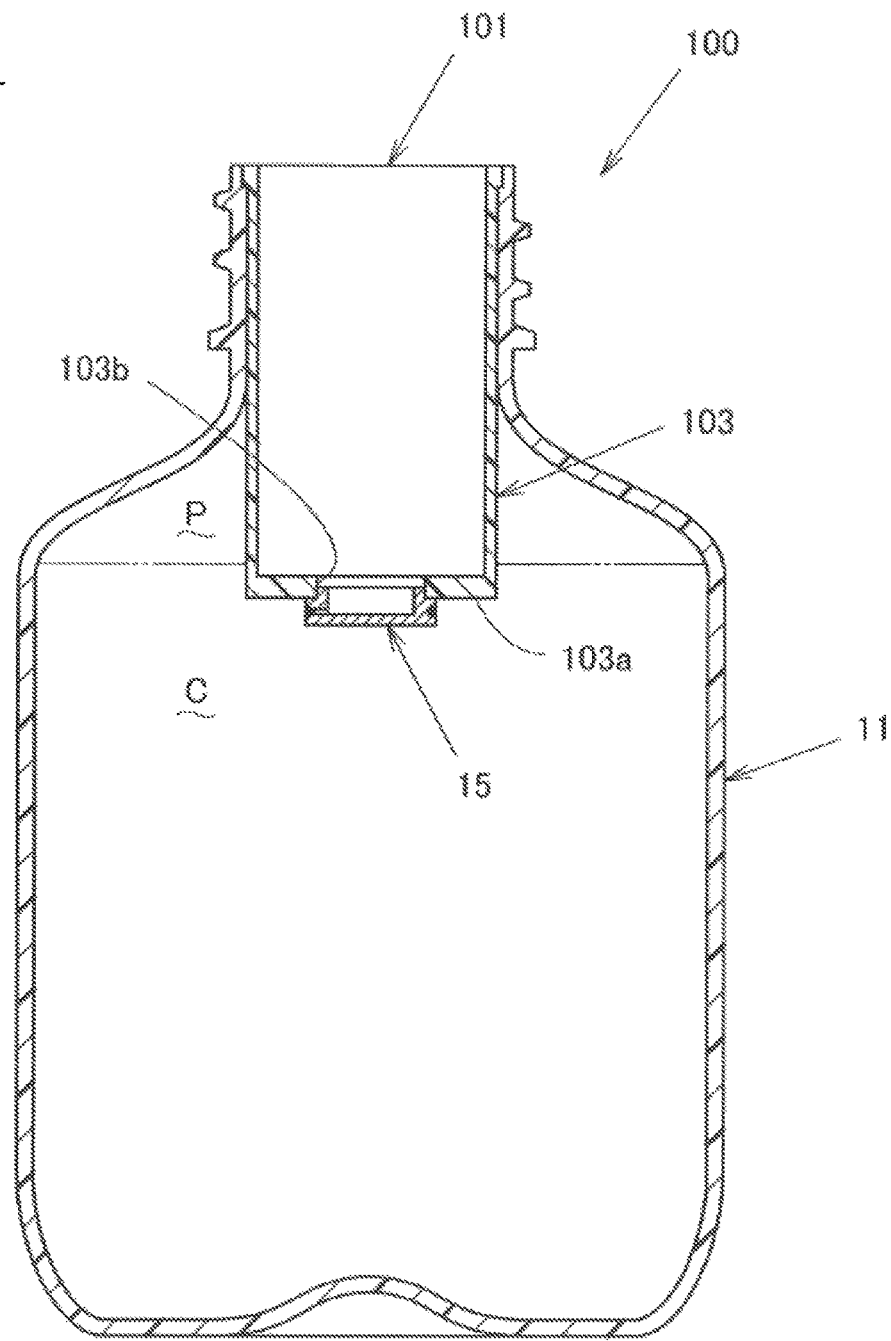
FIG. 11 A cross-sectional view showing further another embodiment of the content-accommodating container of the present invention.

The content-accommodating container 100 of FIG. 11 comprises the container body 11 having an opening in the upper end, and a valve accommodating portion 101 which closes the opening thereof, and is fixed to the container body 11. The valve accommodating portion 101 is provided with a tubular housing portion 103 accommodated in the container body and the closing portion (the first unsealing portion) 15 closing the center hole of a bottom portion 103*a*. The closing portion 15 is that which is same as the closing portion 15 of FIG. 1. This content-accommodating container 100 is different to the content-accommodating container of FIG. 1 in the point that it is not provided with the tube portion. In addition, the concentrate C and the pressurizing agent P is filled so that the lower end of the housing portion 103 dunks in the liquid phase.

The housing portion 103 is a tubular body having a bottom portion 103*a*. In the bottom portion 103*a*, a center hole 103*b* is formed. The connecting portion 15*a* of the closing portion 15 is fitted into this center hole 103*b*. Moreover, in the bottom portion 103*a*, the thin wall portion is not equipped. In the content-accommodating container 100, a discharge device equipped with the dip tube is used. For example, the discharge device 21 of FIG. 2 not equipped with the puncture portion (the discharge device 97 of FIG. 9B), the discharge device 61 of FIG. 6A, and the discharge device 71 of FIG. 6B not equipped with the puncture portion can be cited.

Figure 12:
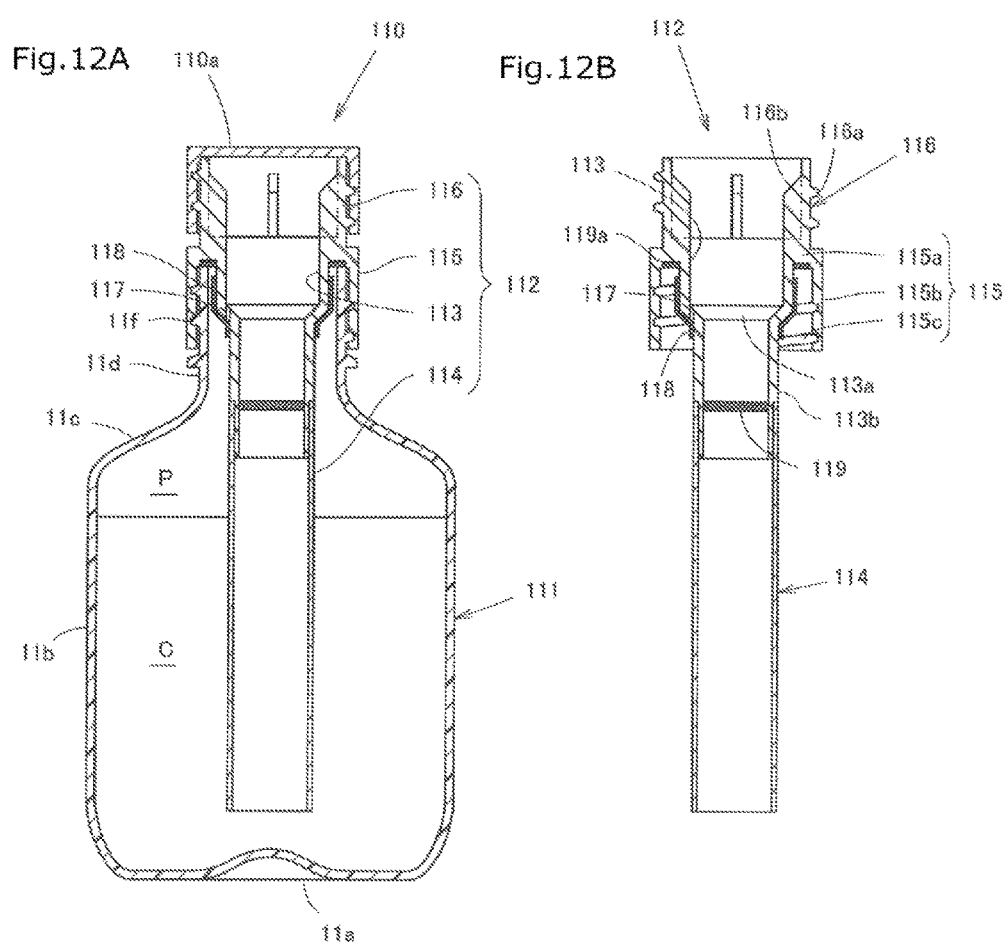
FIG. 12A is a cross-sectional view showing further another embodiment of the content-accommodating container of the preset invention.
FIG. 12B is a cross-sectional view showing the valve accommodating portion thereof.

The content-accommodating container 110 of FIG. 12A is provided with the check valve (the seal material 118) in the gas introducing passage (the gas introducing hole 117). Moreover, the fixing means of a valve accommodating portion 112 to a container body 111 is different from those up till now. In detail, it comprises the container body 111 having an opening in the upper end, and a valve accommodating portion 112 which closes the opening thereof, and is fixed to the container body 111.

Further, a lid portion 110*a* is provided in the upper end of the valve accommodating portion 112. In this content-accommodating container 110, the valve accommodating portion 112 is fixed to the container body 111 by screwing, and the discharge device is screwed to the valve accommodating portion 112. By filling a concentrate and a pressurizing agent in the content-accommodating container 110, it becomes a refill container accommodating product. By attaching a removable valve member (discharge device) having the valve mechanism to this refill content accommodating product, it becomes a discharge product in which the closing portion 119 is unsealed.

The container body 111 is substantially same as the container body 11 of the content-accommodating container 10 of FIG. 1, excepting the point that the step portion 11e to support the upper end of the valve accommodating portion 112 is not formed, and has the bottom portion 11a, the body portion 11b, the shoulder portion 11c, and the neck portion 11d, and in the outer periphery of the neck portion 11d, the male screw 11f is formed.

The valve accommodating portion 112 is provided with a tubular housing portion 113 accommodated inside the container body, a tube portion 114 extending downward from the housing portion 113 and the lower end of which is arranged in the vicinity of the bottom, a valve cap portion 115 provided in the upper end of the housing portion 113, a tubular attaching portion 116 extending upward from the valve cap portion thereof, and a closing portion 119 (first unsealing portion) closing the inside of the housing portion 113. The housing portion 113, the valve cap portion 115, and the attaching portion 116 are tubular bodies made of synthetic resin integrally formed coaxially. The tube portion 114 is attached to the lower end of the housing portion 113. However, it may be integrally formed.

The housing portion 113 is, as shown in FIG. 12B, a tubular body, and in the middle part thereof, a first taper portion (first step portion) 113a reduced in diameter facing downward is formed. A gas introducing hole 117 is formed so as to penetrate the first taper portion 113a. In the outer periphery of the first taper portion 113a, a tubular seal material 118 is provided so as to plug the gas introducing hole 117.

The seal material 118 is that which is of a thin wall tubular shape to be flexibly deformed, and serves as a check valve which allows the fluid flow to the outside (inside of the container body 111) of the housing portion 113, and blocks the fluid flow to the inside (outside air) of the housing portion 113. The first taper portion 113a is provided in order to form the gas introducing hole 117. The lower end of the housing portion 113 is reduced in diameter to compose a tube attaching portion 113b.

In addition, the check valve provided in the gas introducing hole 117 is not limited to the seal material of a tubular thin wall shape having flexibility, and the check valve of another structure (for example, ball valve etc.) may be used.

The valve cap 115 comprises a ring like support portion 115a protruding outward in the radial direction from the upper end of the housing portion 113, and a cylindrical portion 115b extending downward from the outer end thereof so as to cover the outer periphery of the container body 111. The support portion 115a is arranged above the upper end of the container body 111 through the ring like seal material 119a.

In the inner surface of the cylindrical portion 115b, a female screw 115c screwing with the male screw 11f of the container body 111 is formed.

The attaching portion 116 is a cylindrical body extending upward from the upper surface of the support portion 115a of the valve cap portion 115. In the outer periphery thereof, a male screw 116a is formed for being fitted in the discharge device. In the inner surface of the attaching portion 116, a plurality of ribs 116b extending vertically is arranged radially. The inner end of the rib 116b extends up to the same position as the inner diameter of the upper portion of the housing portion 113. Thereby, the inner diameter of the attaching portion 116 and the inner diameter of the housing portion 113 are made to be the same, which act as the guide of the discharge device, when attaching the discharge device.

The closing portion 119 is provided in the lower portion so as to close the tube attaching portion 113b of the housing portion 113. However, the position is not particularly limited as long as it closes the inner surface of the housing portion 113.

The filling method of a concentrate and a pressurizing agent in the content-accommodating container 110 is that, same as the content-accommodating container 80 of FIG. 7A, the concentrate is filled in the container body 111, after that, the pressurizing agent is filled from between the valve accommodating portion 112 and the container body 111, just before the valve accommodating portion is fixed to the container body 111. At the same time as the filling of the pressurizing agent, the valve accommodating portion 112 is attached to the container body 111 by screwing. Moreover, the concentrate is filled in the container body 111, the valve accommodating portion 112 is inserted and fixed, after that, the pressurizing agent may be filled through the gas introducing portion 117 of the housing portion 113 while opening the seal material 118. After assembling the content-accommodating container 110, the concentrate and the pressurizing agent may be filled through the gas introducing portion 117 while opening the seal material 118.

Figure 13:
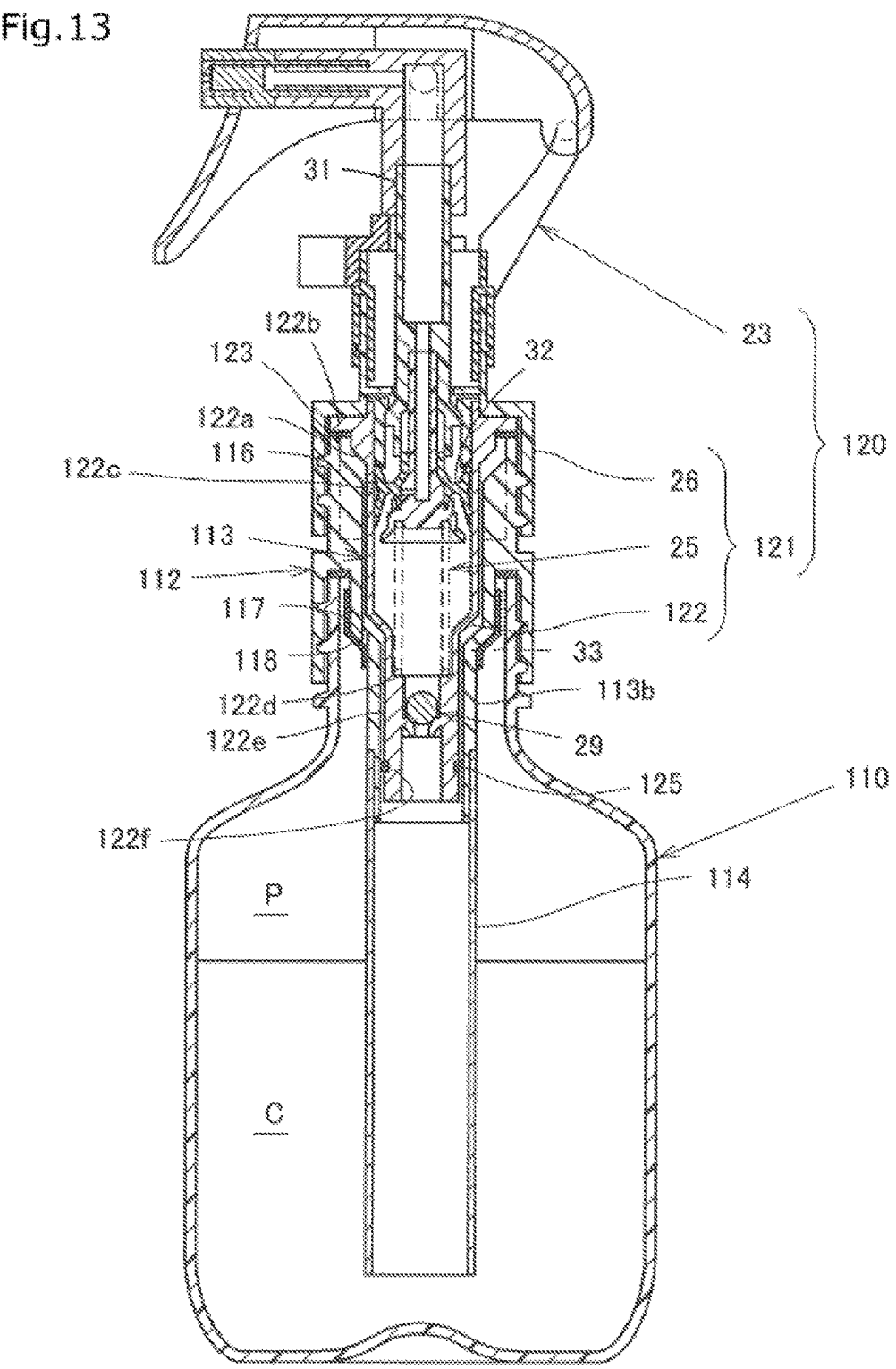
FIG. 13 A cross-sectional view showing further another aspect of the discharge product of the preset invention.

The discharge device of FIG. 13 comprises the content-accommodating container 110 of FIG. 12A, the concentrate C and the agent P filled therein, and a discharge device 120 attached to the content-accommodating container 110.

The discharge device 120 is provided with a valve member 121 equipped with the valve mechanism 25, the operating member 23 attached to the valve member 121 for operating the valve mechanism 25. The operating member 23 is that which is same as the discharge device 21 of FIG. 2. The valve member 121 comprises a tubular valve housing 122, the valve mechanism 25 accommodated inside thereof, and the cap 26 which fixes the valve mechanism 25 to the inside of the valve housing 122, and fixes the valve housing 122 to the content-accommodating container 110. The valve mechanism 25 and the cap 26 is that which is substantially same as the discharge device 21 of FIG. 2. In addition, the cap 26 is attached to the attaching portion 116 of the valve accommodating portion 112, not to the container body 111.

The valve housing 122 is a tubular body reduced in diameter facing downward. In the upper portion, a taper portion 122a protruding outward in the radial direction facing upward is formed, in the upper end thereof, a flange portion 122b protruding outward in the radial direction is formed. The flange portion 122b is arranged above the attaching portion 116 of the valve accommodating portion 112 through the ring like seal material 123. In the upper side surface below the taper portion 122a, a gas phase communicating hole 122c is formed. The gas phase communicating hole 122c is opened and closed by the piston 32 of the valve mechanism 25. In the lower portion, a step portion 122d to support the spring 33 of the valve mechanism 25 is formed. The lower portion thereof is made to be a tube portion 122e reduced in diameter extending downward. The lower end of the tube portion 122e is made to be the liquid phase communicating hole. Moreover, inside the tube portion 122e, the check valve 29 is provided. The check valve 29 is substantially the same ball valve as the check valve 29 of the discharge device 21 of FIG. 2.

On the other hand, in the exterior of the tube portion 122e, an annular recessed portion 122f to hold the seal material (O ring member) 125 is formed. This seal material 125 is compressed between the inner surface of a tube attaching portion 113b of the housing portion 113 and the bottom surface of the annular recessed portion 122f and seals between the valve accommodating portion 112 and the valve member 121. By providing this seal material 125, it becomes possible to unseal the first unsealing portion 119 while sealing between the valve accommodating portion 112 and the valve member 121, when attaching the discharge device 120 to the content-accommodating portion 110, making it possible to prevent further the pressurizing agent and the concentrate from leaking out.

Since in this content-accommodating portion 110, the seal material 118 to exert the effect of a check valve is provided in the gas introducing hole 117, even if the stem 31 of the discharge device 120 is lowered more than a certain mount, and being switched to the pump discharge state, the pressurizing agent P of the content-accommodating product is never discharged to the exterior through the gas introducing portion (the gas introducing hole 117) of the valve accommodating portion, and the gas phase communicating hole 122c of the valve member. In addition, in the case that the gas phase portion of the container body 111 becomes negative pressure in regard to the exterior by discharging the contents, when the stem 31 is lowered more than a certain amount, air is introduced into inside the valve accommodating portion 112 from outside through the gas phase communicating hole 122c of the valve member 121, the seal material 118 opens the gas introducing hole 117 to supply air to the gas phase portion of the container body 111.

Hence, even if the stem 31 is lowered too much in error, the content can be aerosol-discharged after that. In other words, it can be efficiently used without exhausting the pressurizing agent. In addition, in this case, that which controls the lowering amount of the stem of the operation switching member 20a etc. of FIG. 5 is not necessary, but may be provided.

The content-accommodating container 130 of FIG. 14A is substantially same as the content-accommodating container 110 of FIG. 12A excepting the point that the first unsealing portion 119 is provided in the lower end of the tube portion 114 of the valve accommodating portion 112.

The discharge device 131 of FIG. 14B comprises the content-accommodating container 130 of FIG. 14A, the concentrate C and the pressurizing agent P filled therein, and a discharge device 132 attached to the content-accommodating container 130. The discharge device 132 is substantially same as the discharge device 120 of FIG. 13 excepting the point that a dip tube 133 is provided in the tubular portion 122e of the valve housing 122, and that the ring like seal material 123 provided between the flange portion 122b of the valve housing 122b and the attaching portion 116 of the valve accommodating portion 112 is arranged between the outer periphery of the valve housing 122 and the inner surface of the attaching portion 116, and is the seal material 133 (O ring) compressed in the radial direction. By using the seal material 133 compressed in the radial direction, it becomes possible to secure salability even if the attaching of the discharge device 132 and the content-accommodating container 130 is somewhat loose.

However, this seal structure is no more than an embodiment and is not particularly limited.

The discharge product 135 of FIG. 14C comprises a content-accommodating container 136, the concentrate C and the pressurizing agent P filled therein, and a discharge device 132 of FIG. 14B attached to the content-accommodating container 136. In the discharge device 132, the operation switching member 20a of the discharge device 21 of FIG. 2 is provided.

The content-accommodating container 136 is a container not having the valve accommodating portion, and it is not particularly limited as long as it is constituted so that the discharge device 132 can be attached. Here, in the periphery of the mouth portion of the content-accommodating container 136, a male screw 136a screwing with the cap 26 of the valve member 121 of the discharge device 132 is formed.

In this discharge device 135, the gas phase of the content-accommodating container 136 and the valve housing 122 of the discharge device 132 are communicated by the gas phase communicating hole 122c opened and closed by the piston 32. Hence, if the auxiliary pump mechanism is operated, the pressurizing agent of the content-accommodating container 136 is exhausted outside through the gas phase communicating hole 122c. Hence, the operation switching member 20a is provided for preventing wrong operation.

In this way, as the primal product, it is possible to lower the cost as much as the cost of the valve accommodating portion, by selling the product as the discharge product 135 comprising the content-accommodating container 136 not equipped with the valve accommodating portion and the discharge device 132. On the other hand, as the refill product, the content-accommodating container 130 of FIG. 14A is used. In the discharge product 132 of FIG. 14B, users attach the discharge product 132 to the refill content-accommodating container 130 to use. Thereby, it becomes possible to reuse the discharge device 132.

The content-accommodating container 140 of FIG. 15A is substantially same as the content-accommodating container 130 of FIG. 14A other than that the position of the first unsealing portion 119 and the gas introducing hole 117 is different. In detail, the first unsealing portion 119 is provided above the tube portion 114, the gas introducing hole 117 is formed lower than the first unsealing portion 119. The discharge product 145 of FIG. 15B comprises the content-accommodating container 140 of FIG. 14A, the concentrate C and the pressurizing agent P filled therein, and the discharge device 142 attached to the content-accommodating container 140

In the discharge device 142, a seal material 143 is provided in the outer periphery of the housing body 122 so as to plug the gas phase communicating portion 122c. This seal material 143 comprises a thin wall tubular elastic body, and acts also as a check valve which allows the fluid flow from the inside of the housing body 122 to the exterior, and blocks the fluid flow from the exterior to the interior. Hence, even if the stem 31 of the discharge device 142 is lowered more than a prescribed amount and the pump discharge state is switched, the pressurizing agent of the content-accommodating product is never exhausted through the gas phase communicating hole 122c.

In addition, the check valve provided in the gas phase communicating portion 122c is not also limited to the seal material 143, but the check valve of another structure (for example, ball valves etc.) may be used.

Moreover, the ring like seal material 145 arranged between the flange portion 122b of the housing portion 122 and the attaching portion 116 of the valve accommodating portion 112 is U-shaped so as to cover the upper end of the attaching portion 116. In other words, the seal material 145 comprises an inside seal portion 145a, an outside seal portion 145b and an upper side seal portion 145c connecting the upper end of those. The inside seal portion 145a is compressed between the outer surface of the housing body 122 and the inner surface of the attaching portion 116 in the radial direction, the outside seal portion 145b is compressed between the inner surface of the cap 26 and the outer surface of the attaching portion 116 in the radial direction, the upper side seal portion 145c is compressed between the lower surface of the cap 26 and the upper surface of the attaching portion 116 in the vertical direction. As described above, an annular line seal structure is formed in three directions, the sealability becomes high. In addition, the inside seal portion 145a is made to be thicker than the outside seal portion 145b and the upper side seal portion 145c, the degree of compression thereof becomes high. However, this seal structure is no more than an embodiment, and is not particularly limited.

Another composition is substantially same as the discharge device 132 of FIG. 14, the O ring 125 is provided below the valve housing 122, the lower end 122g (the first unsealing portion) of the valve housing 122 is made to be sharp-edged so as to be capable of breaking the first closing portion 119.

In the discharge product 145, when the discharge device 142 is attached to the content-accommodating container 140, before unsealing the first unsealing portion 119, between the tube portion 114 of the valve accommodating portion 112 of the content-accommodating container 140 and the valve housing 122 of the discharge device 142 is sealed by the O ring, after the unsealing portion 119 is unsealed, the O ring 125 moves up to the position lower than the gas introducing hole 117 of the tube portion 114, the gas introducing hole 117 communicates the gap between the gas phase of the content-accommodating container 140 and the valve housing 122 and the valve accommodating portion 112. Hence, in the case that the stem 31 is lowered more than a certain amount in the state that the gas phase portion of the content-accommodating container 140 becomes negative pressure in regard to the exterior, the seal material 143 opens to introduce air into inside the content-accommodating container 140 from the exterior, through the gas phase communicating portion 122c of the valve member, the gas introducing portion 117.

The discharge product 148 of FIG. 15D comprises the content-accommodating container 136 of FIG. 14C, the concentrate C and the pressurizing agent P filled therein, and the discharge device 142 of FIG. 15B. Since in this discharge product 148, different to the discharge product 135 of FIG. 14C, since the check valve is provided in the gas phase communicating portion 122c of the housing body 122, even if the stem 31 is lowered more than a certain amount, the pressurizing agent is never exhausted.

What is claimed is:

1. A discharge product comprising a content-accommodating product which is used by attaching a removable valve member having a valve mechanism, and a discharge device attached to the content-accommodating product,
wherein the content-accommodating product comprises a content-accommodating container, and a concentrate and a compressed gas or a liquid gas filled in the content-accommodating container,
wherein the content-accommodating container comprises a container body having an opening, and a tubular valve accommodating portion for accommodating the valve mechanism, wherein the valve accommodating portion is fixed to the container body and closes the opening of the container body, wherein the valve accommodating portion has a communicating portion to communicate with a liquid phase of the container body and a first unsealing portion to close the communicating portion,
wherein the discharge device is provided with the valve member comprising a valve housing accommodated in the valve accommodating portion, the valve mechanism accommodated in the valve housing, and a cap which fixes the valve housing to the content-accommodating container, wherein the cap is fixed to the valve accommodating portion, and wherein the valve housing has a lower end to unseal the first unsealing portion of the content-accommodating container.

2. The discharge product according to claim 1, wherein the valve mechanism is an aerosol valve mechanism which comprises a stem, a stem rubber closing the stem hole thereof, and a spring energizing the stem upward.

3. The discharge product according to claim 2, wherein the valve mechanism is provided with an auxiliary pump mechanism to compress a storing space of the concentrate inside the valve housing.

4. The discharge product according to claim 3, wherein the auxiliary pump mechanism comprises the valve housing and a piston which slides inside the valve housing in conjunction with the stem, when the stem of the aerosol valve mechanism is pushed down more than a prescribed amount.

5. The discharge product according to claim 4, wherein a gas phase communicating hole which communicates the gas phase of the container body with outside air is formed in the valve housing, and wherein the gas phase communicating hole is closed by the piston, when the auxiliary pump mechanism is not operating, and is opened by the operation of the piston.

6. The discharge product according to claim 3, further comprising a switch to operate the auxiliary pump mechanism.

7. The discharge product according to claim 1, further comprising a seal material which is compressed between the outer surface of the valve housing and an inner surface of the valve accommodating portion.

8. The discharge product according to claim 1, further comprising a seal material which is compressed between the cap and an upper end of the container body.

* * * * *